US009102958B2

(12) United States Patent
Botes et al.

(10) Patent No.: US 9,102,958 B2
(45) Date of Patent: Aug. 11, 2015

(54) METHODS OF PRODUCING 6-CARBON CHEMICALS VIA COA-DEPENDENT CARBON CHAIN ELONGATION ASSOCIATED WITH CARBON STORAGE

(71) Applicant: INVISTA North America S.a r.l., Wilmington, DE (US)

(72) Inventors: Adriana L. Botes, Cleveland (GB); Alex Van Eck Conradie, Cleveland (GB)

(73) Assignee: INVISTA North America S.á.r.l., Wilmington, DE (US)

( * ) Notice: Subject to any disclaimer, the term of this patent is extended or adjusted under 35 U.S.C. 154(b) by 0 days.

(21) Appl. No.: 13/715,981

(22) Filed: Dec. 14, 2012

(65) Prior Publication Data

US 2013/0183728 A1 Jul. 18, 2013

Related U.S. Application Data

(60) Provisional application No. 61/576,401, filed on Dec. 16, 2011.

(51) Int. Cl.
| | | |
|---|---|---|
| C12P 7/18 | (2006.01) | |
| C12P 7/44 | (2006.01) | |
| C12P 17/10 | (2006.01) | |
| C12N 15/52 | (2006.01) | |
| C12P 7/42 | (2006.01) | |
| C12P 13/00 | (2006.01) | |

(52) U.S. Cl.
CPC . *C12P 7/44* (2013.01); *C12N 15/52* (2013.01); *C12P 7/18* (2013.01); *C12P 7/42* (2013.01); *C12P 13/001* (2013.01); *C12P 13/005* (2013.01); *C12P 17/10* (2013.01)

(58) Field of Classification Search
None
See application file for complete search history.

(56) References Cited

U.S. PATENT DOCUMENTS

| | | | |
|---|---|---|---|
| 2,439,513 | A | 4/1948 | Hamblet et al. |
| 2,557,282 | A | 6/1951 | Hamblet et al. |
| 2,791,566 | A | 5/1957 | Jeffers |
| 2,840,607 | A | 6/1958 | Attane, Jr. et al. |
| 2,971,010 | A | 2/1961 | Gilby, Jr. et al. |
| 3,023,238 | A | 2/1962 | Chapman et al. |
| 3,338,959 | A | 8/1967 | Sciance et al. |
| 3,365,490 | A | 1/1968 | Arthur et al. |
| 3,515,751 | A | 6/1970 | Oberster |
| 3,719,561 | A | 3/1973 | Tanaka et al. |
| 4,058,555 | A | 11/1977 | Mims |
| 6,255,451 | B1 | 7/2001 | Koch et al. |
| 6,372,939 | B1 | 4/2002 | Bunel et al. |
| 8,088,607 | B2 | 1/2012 | Buggard et al. |
| 2004/0054235 | A1 | 3/2004 | Fodor et al. |
| 2010/0035309 | A1 | 2/2010 | Havemen et al. |
| 2010/0151536 | A1 | 6/2010 | Baynes et al. |
| 2010/0203600 | A1 | 8/2010 | Dubois |
| 2011/0171699 | A1 | 7/2011 | Raemakers-Franken et al. |
| 2011/0256599 | A1 | 10/2011 | Hu et al. |
| 2012/0064252 | A1 | 3/2012 | Beatty |
| 2012/0101009 | A1 | 4/2012 | Beatty |
| 2013/0065279 | A1 | 3/2013 | Burk et al. |
| 2013/0210090 | A1 | 8/2013 | Pearlman et al. |
| 2013/0217081 | A1 | 8/2013 | Pearlman et al. |
| 2013/0224807 | A1 | 8/2013 | Pearlman et al. |
| 2014/0186902 | A1 | 7/2014 | Botes et al. |
| 2014/0186904 | A1 | 7/2014 | Botes et al. |
| 2014/0193861 | A1 | 7/2014 | Botes et al. |
| 2014/0193862 | A1 | 7/2014 | Botes et al. |
| 2014/0193863 | A1 | 7/2014 | Botes et al. |
| 2014/0193864 | A1 | 7/2014 | Botes et al. |
| 2014/0193865 | A1 | 7/2014 | Botes et al. |
| 2014/0196904 | A1 | 7/2014 | Fontenelle et al. |
| 2014/0199737 | A1 | 7/2014 | Botes et al. |
| 2014/0248673 | A1 | 9/2014 | Botes et al. |

FOREIGN PATENT DOCUMENTS

| | | | |
|---|---|---|---|
| WO | WO 2008/006037 | 1/2008 | |
| WO | WO 2008/145737 | 12/2008 | |
| WO | WO 2009/113855 | 9/2009 | |
| WO | WO 2009/140695 | 11/2009 | |
| WO | WO 2009/140696 | 11/2009 | |
| WO | WO 2009/151728 | 12/2009 | |
| WO | WO2009151728 | * 12/2009 | ............. C12P 17/10 |
| WO | WO 2010/068944 | 6/2010 | |
| WO | WO 2010/068953 | 6/2010 | |
| WO | WO 2010/071759 | 6/2010 | |

(Continued)

OTHER PUBLICATIONS

Dekishima"Extending Carbon Chain Length of 1-Butanol Pathway for 1-Hexanol Synthesis from Glucose by Engineered *Escherichia coli*" J. Am. Chem. Soc. 2011, 133, 11399-11401.*

Fuhhoff "CYP153A6, a Soluble P450 Oxygenase Catalyzing Terminal-Alkane Hydroxylation"Journal of Bacteriology, Jul. 2006, p. 5220-5227.*

Iwaki "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them"Applied and Environmental Microbiology.*

(Continued)

*Primary Examiner* — Suzanne M Noakes
*Assistant Examiner* — Gerard Lacourciere
(74) *Attorney, Agent, or Firm* — Fish & Richardson P.C.

(57) ABSTRACT

This document describes biochemical pathways for producing adipic acid, caprolactam, 6-aminohexanoic acid, hexamethylenediamine or 1,6-hexanediol by forming two terminal functional groups, comprised of carboxyl, amine or hydroxyl groups, in a C6 aliphatic backbone substrate. These pathways, metabolic engineering and cultivation strategies described herein rely on CoA-dependent elongation enzymes or analogues enzymes associated with the carbon storage pathways from polyhydroxyalkanoate accumulating bacteria.

56 Claims, 6 Drawing Sheets

(56) References Cited

FOREIGN PATENT DOCUMENTS

| WO | WO 2010/104390 | 9/2010 |
|----|----|----|
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/082542 | 6/2013 |
| WO | WO 2013/090837 | 6/2013 |
| WO | WO 2013/096898 | 6/2013 |
| WO | WO 2014/105788 | 7/2014 |

OTHER PUBLICATIONS

Larroy "Characterization of the *Saccharomyces cerevisiae* YMR318C (ADH6) gene product as a broad specificity NADPH-dependent alcohol dehydrogenase: relevance in aldehyde reduction" Biochem. J. (2002) 361, 163±172.*
Zhuang "Divergence of Function in the Hot Dog Fold Enzyme Superfamily: The Bacterial Thioesterase YciA"Biochemistry 2008, 47, 2789-2796.*
http://www.brenda-enzymes.org/php/result_flat.php4?ecno=1.2.1.57.*
http://biocyc.org/EFAE226185/NEW-IMAGE?type=ENZYME&object=GHI1-877-MONOMER.*
International Search Report and Written Opinion for International Application No. PCT/US2012/069934, mailed Jan. 17, 2014, 21 pages.
"Brenda—The comprehensive Enzyme Information System," Oct. 2, 2011, retrieved on Mar. 14, 2013, http://web.archive.org/web/20111002145.
Barker et al., "Enzymatic reactions in the degradation of 5-aminovalerate by *Clostridium aminovalericum*," *J. Biol. Chem.*, 1987, 262(19):8994-9003.
Becker et al., "Metabolic flux engineering of L-lysine production in *Corynebacterium glutamicum*—over expression and modification of G6P dehydrogenase," *J. Biotechnol.*, 2007, 132:99-109.
Bellmann et al., "Expression control and specificity of the basic amino acid exporter LysE of *Corynebacterium glutamicum*," *Microbiology*, 2001, 147:1765-1774.
Bond-Watts et al., "Biochemical and structural characterization of the trans-enoyl-CoA reductase from *Treponema denticola*," *Biochemistry*, 2012, 51:6827-6837.
Brigham et al., *Advanced Biofuels and Bioproducts*, 2012, Chapter 39, pp. 1065-1090.
Budde et al., "Roles of Multiple Acetoacetyl Coenzyme A Reductases in Polyhydroxybutyrate Biosynthesis in *Ralstonia eutropha* H16," *J. Bacteriol.*, 2010, 192(20):5319-5328.
Bugg et al., "The emerging role for bacteria in lignin degradation and bio-product formation," *Curr. Opin. in Biotechnol.*, 2011, 22:394-400.
Cantu et al., "Thioesterases: a new perspective based on their primary and tertiary structures," *Protein Science*, 2010, 19:1281-1295.
Davis et al., "Overproduction of acetyl-CoA carboxylase activity increases the rate of fatty acid biosynthesis in *Escherichia coli*," *J. Biol. Chem.*, 2000, 275(37): 28593-28598.
Dekishima et al., "Extending Carbon Chain Length of 1-Butanol Pathway for 1-Hexanol Synthesis from Glucose by Engineered *Escherichia coli*," *J. Am. Chem. Soc.*, Aug. 2011, 133(30):11399-11401.
Elkins & Nikaido, "Substrate specificity of the RND-type multidrug efflux pumps AcrB and AcrD of *Escherichia coli* is determined predominantly by two large periplasmic loops," *J. Bacteriol.*, 2002, 18423:6490-6499.
Fukui et al., "Expression and characterization of (R)-specific enoyl coenzyme A hydratase involved in polyhydroxyalkanoate biosynthesis by *Aeromonas caviae*," *J. Bacteriol.*, 1998, 180(3):667-673.
Funhoff et al., "Expression and Characterization of (R)-Specific Enoyl Coenzyme A Hydratase Involved in Polyhydroxyalkanoate Biosynthesis by *Aeromonas caviae*," *J. Bacteriol.*, 2006, 188(14):5220-5227.
GenBank Accession No. AAA24665.1.
GenBank Accession No. ABK71854.1.
GenBank Accession No. ACC40567.1.
GenBank Accession No. EFV11917.1.
GenBank Accession No. EIV11143.1.
GenBank Accession No. ADG98140.1.
GenBank Accession No. AAQ59697.1.
GenBank Accession No. AAG08191.1.
GenBank Accession No. AAY39893.1.
GenBank Accession No. ABA81135.1.
GenBank Accession No. AAA57874.1.
GenBank Accession No. AEA39183.1.
GenBank Accession No. ABE47160.1.
GenBank Accession No. CAH04396.1.
GenBank Accession No. ACJ06772.1.
GenBank Accession No. ABE47159.1.
GenBank Accession No. CAH04397.1.
GenBank Accession No. ABE47158.1.
GenBank Accession No. CAH04398.1.
GenBank Accession No. CAA44858.1.
GenBank Accession No. ABI83656.1.
GenBank Accession No. AAA69178.1.
GenBank Accession No. CAA81612.1.
Gloerich et al., "Peroxisomal trans-2-enoyl-CoA reductase is involved in phytol degradation," *FEBS Letters*, 2006, 580:2092-2096.
Guerrillot and Vandecasteele, "Purification and characterization of two aldehyde dehydrogenases from *Pseudomonas aeruginosa*," *Eur. J. Biochem.*, 1977, 81:185-192.
Harwood and Parales, "The beta-ketoadipate pathway and the biology of self-identity," *Ann. Rev. Microbiol.*, 1996, 50:553-590.
Haywood et al., "Characterization of two 3-ketothiolases possessing differing substrate specificities in the polyhydroxyalkanoate synthesizing organism *Alcaligenes eutrophus*," *FEMS Microbiology Letters*, 1988, 52:91-96.
Hermann et al, "Industrial production of amino acids by coryneform bacteria," *J. Biotechnol.*, 2003, 104:155-172.
Ho and Weiner, "Isolation and characterization of an aldehyde dehydrogenase encoded by the aldB gene of *Escherichia coli*," *J. Bacteriol.*, 2005, 187(3):1067-1073.
Huhn et al., *Appl. Microbiol. & Biotech.*, YR, 89(2):327-335.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," *Appl. Environ. Microbiol.*, 1999, 65(11):5158-5162.
Jang et al., "Bio-based production of C2-C6 platform chemicals," *Biotechnol. & Bioengineering*, 2012, 109(10):2437-2459.
Jarboe, "YqhD: a broad-substrate range aldehyde reductase with various applications in production of biorenewable fuels and chemicals," *Appli Micorbiol. Biotechnol.*, 2011, 89(2):249-257.
Jaremko and Yu, "The initial metabolic conversion of levulinic acid in *Cupriavidus necator*," *J. Biotechnol.*, 2011, 155:293-298.
Kaulmann et al., "Substrate spectrum of ω-transaminase from *Chromobacterium violaceum* DSM30191 and its potential for biocatalysis," *Enzyme and Microbial Technology*, 2007, 41:628-637.
Kim, "Purification and Properties of a mine α-Ketoglutarate Transaminase from *Escherichia coli*," *J. Chem.*, 1963, 239(3):783-786.
Koch et al., "In Vivo Evolution of Butane Oxidation by Terminal Alkane Hydroxylases AlkB and CYP153A6," *Appl. Environ. Microbiol.*, 2009, 75(2):337-344.
Köpke et al., "2,3-butanediol production by acetogenic bacteria, an alternative route to chemical synthesis, using industrial waste gas," *Appl. and Environ. Microbiol.*, 2011, 77(15):5467-5475.

(56) References Cited

OTHER PUBLICATIONS

Kulkarni and Kanekar, "Bioremediation of epsilon-caprolactam from nylon-6 waste water by use of *Pseudomonas aeruginosa* MCM B-407," *Curr. Microbiol.*, 1998, 37:191-194.
Larroy et al., "Characterization of the *Saccharomyces cerevisiae* YMR318C (ADH6) gene product as a broad specificity NADPH-dependent alcohol dehydrogenase: relevance in aldehyde reduction," *J. Biochem.*, 2002, 361(1):163-172.
Lee et al., "Metabolic Engineering of Pentose Phosphate Pathway in Ralstoniaeutropha for EHenhanced Biosynthesis of Poly-β-hydroxybutyrate," *Biotechnology Progress*, 2003, 19(5):1444-1449.
Lee et al., "Synthesis of Pure meso-2,3-Butanediol from Crude Glycerol Using an Engineered Metabolic Pathway in *Escherichia coli*," *Appl. Biochem. Biotechnol.*, 2012, 166(7):1801-1813.
Li et al., "*Cupriavidus necator* JMP134 rapidly reduces furfural with a Zn-dependent alcohol dehydrogenase," *Biodegradation*, 2011, 22(6):1215-1225.
Lim et al., "Amplification of the NADPH-related genes zwf and gnd for the oddball biosynthesis of PHB in an *E. coli* transformant harboring a cloned phbCAB operon," *J. Bioscience and Bioengineering*, 2002, 93(6):543-549.
Liu and Chen, "Production and characterization of medium-chain-length polyhydroxyalkanoate with high 3-hydroxytetradecanoate monomer content by fadB and fadA knockout mutant of *Pseudomonas putida* KT2442,"*Appl. Microbiol. Biotechnol.*, 2007, 76(5):1153-1159.
Lopez-Sanchez et al., "Tetralin-Induced and ThnR-Regulated Aldehyde Dehydrogenase and β-Oxidation Genes in *Sphingomonas macrogolitabida* Strain TFA," *Appl. Environ. Microbiol.*, 2010, 76(1):110-118.
Lutke-Eversloh and Steinbuchel, Biochemical and molecular characterization of a succinate semialdehyde dehydrogenase involved in the catabolism of 4-hydorxybutyric acid in *Ralstonia eutropha, FEMS Microbiol. Letters*, 1999, 181(1)63-71.
Martin and Prather, "High-titer production of monomeric hydroxyvalerates from levulinic acide *Pseudomonas putida*," *J. Biotechnol.*, 2009, 139: 61-67.
Matsumoto et al., "A new pathway for poly(3-hydroxybutyrate) production in *Escherichia coli* and *Corynebacterium glutamicum* by functional expression of a new acetoacetyl-coenzyme A synthase," *Biosci. Biotechnol. Biochem.*, 2011, 75(2):364-366.
Meijnen et al., "Improved p-hydroxybenzoate production by engineered *Pseudomonas putida* S12 by using a mixed-substrate feeding strategy," *Appl. Microbiol. Biotechnol.*, 2011, 90:885-893.
Mo et al., "Connecting extracellular metabolomic measurements to intracellular flux states in yeast," *BMC Systems Biology*, 2009, 3(37):1-17.
Naggert et al., "Cloning, sequencing, and characterization of *Escherichia coli* thioesterase II," *J. Biol. Chem.*, 1991, 266(17):11044-11050.
Neyfakh, "The Multidrug Efflux Transporter of *Bacillus subtilis* is a Structural and Functional Homolog of the *Staphylococcus* NorA Protein," *Antimicrob Agents Chemother*, 1992, 36(2):484-485.
Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," *J. Biochem.*, 1984, 95:1315-1321.
Ng et al., "Quinolone Resistance Mediated by norA: Physiologic Characterization and Relationship to flqB, a Quinolone Resistance Locus on the *Staphylococcus aureus* Chromosome," *Antimicrob Agents Chemother*, 1994, 38(6):1345-1355.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," *Appl. Environ. Microbiol.*, 2005, 71(8):4297-4306.
Ohashi et al., "Continuous production of lactic acid from molasses by perfusion culture of *Lactococcus lactis* using a stirred ceramic membrane reactor," *J. Bioscience and Bioengineering*, 1999, 87(5):647-654.

Okuhara et al., "Formation of Glutaric and Adipic Acids from n-Alkanes with Odd and Even Numbers of Carbons by *Candida tropicalis* OH23," *Agr. Biol. Chem.*, 1971, 35(9):1376-1380.
Palosaari and Rogers, "Purification and properties of the inducible coenzyme A-linked butyraldehyde dehydrogenase from *Clostridium acetobutylicum*," *J. Bacteriol.*, 1988, 170(7):2971-2976.
Papanikolaou et al., "Citric acid production by *Yarrowia lipolytica* cultivated on olive-mill wastewater-based media," *Bioresource Technol.*, 2008, 99(7):2419-2428.
Pérez-Pantoja et al., "Metabolic reconstruction of aromatic compounds degradation from the genome of the amazing pollutant-degrading bacterium *Cupriavidus necator* JMP134," *FEMS Microbiol. Rev.*, 2008, 32:736-794.
Prybylski et al., "Third-generation feed stocks for the clean and sustainable biotechnological production of bulk chemicals: synthesis of 2-hydroxyisobutyric acid," *Energy, Sustainability and Society*, 2012, 2:11-19.
Rajashekhara and Watanabe, "Propionyl-coenzyme A synthetases of *Ralstonia solanacearum* and *Salmonella choleraesuis* display atypical kinetics," *FEBS Letters*, 2004, 556:143-147.
Ramsay et al., "Use of a Nylon Manufacturing Waste as an Industrial Fermentation Substrate," *Appl. Environ. Microbiol.*, 1986, 52(1):152-156.
Samsonova et al., "Molecular cloning and characterization of *Escherichia coli* K12 ygjG Gene," *BMC Microbiology*, 2003, 3:2.
Sanders et al., "Evidence for two enzymatic pathways for ω-oxidation of docosanoic acid in rat liver microsomes," *J. Lipid Research*, 2005, 46(5):1001-1008.
Sanders et al., "Characterization of the human ω-oxidation pathway for ω-hydroxy-very-long-chain fatty acids," *FASEB Journal*, 2008, 22(6):2064-2071.
Satoh et al., "Enzyme-catalyzed poly(3-hydroxybutyrate) synthesis from acetate with CoA recycling and NADPH regeneration in Vitro," *J. Bioscience and Bioengineering*, 2003, 95(4):335-341.
Scheller et al., "Generation of the soluble and functional cytosolic domain of microsomal cytochrome P450 52A3," *J. Biol. Chem.*, 1994, 269(17):12779-12783.
Seedorf et al., "The genome of *Clostridium kluyveri*, a strict anaerobe with unique metabolic features," *Proc. Natl. Acad. Sci. USA*, 2008, 105(6):2128-2133.
Shen et al., "Driving Forces Enable High-Titer Anaerobic 1-Butanol Synthesis in *Escherichia coli*," *Appl. Environ. Microbiol.*, 2011, 77(9):2905-2915.
Slater et al., "Multiple β-Ketothiolases Mediate Poly(β-Hydroxyalkanoate) Copolymer Synthesis in *Ralstonia eutropha*," *J. Bacteriol.*, 1998, 180(8):1979-1987.
Suzuki et al, "Acetylputrescine deacetylase from *Micrococcus luteus* K-11," *BBA—General Subjects*, 1986, 882(1):140-142.
Suzuki et al., "GriC and GriD Constitute a Carboxylic Acid Reductase Involved in Grixazone Biosynthesis in *Streptomyces griseus*," *J. Antibiot.*, 2007, 60(6):380-387.
Van Beilen and Funhoff, "Expanding the alkane oxygenase toolbox: new enzymes and Applications," *Curr. Opin. Biotechnol.*, 2005, 16:308-314.
Venkitasubramanian et al., "Aldehyde Oxidoreductase as a biocatalyst: Reductions of vanillic acid," *Enzyme and Microbial Technology*, 2008, 42:130-137.
Wee et al., "Biotechnological Production of Lactic Acid and Its Recent Applications," *Food Technol. Biotechnol.*, 2006, 44(2):163-172.
Woolridge et al., "Efflux of the Natural Polyamine Spermidine Facilitated by the *Bacillus subtilis* Multidrug Transporter Blt," *J. Biol. Chem*, 1997, 272(14):8864-8866.
Yang et al., "Value-added uses for crude glycerol-a byproduct of biodiesel production," *Biotechnology for Biofuels*, 2012, 5:13.
Yonaha et al., "4-Aminobutyrate : 2-oxoglutarate aminotransferase of *Streptomyces griseus*: Purification and properties," *Eur. J. Biochem.*, 1985, 146:101-106.
Zhuang et al., "Divergence of Function in the Hotdog-Fold Enzyme Superfamily: The Bacterial Thioesterase YciA," *Biochemistry*, 2008, 47(9):2789-2796.

(56) References Cited

OTHER PUBLICATIONS

Zomorrodi et al., "Improving the iMM904 *S. Cerevisiae* metabolic model using essentiality and synthetic lethality data," *BMC Systems Biology*, Dec. 2010, 4(1):1-15.

Alber et al., "Malonyl-coenzyme A reductase in the modified 3-hydroxypropionate cycle for autotrophic carbon fixation in archaeal *Metallosphaera* and *Sulfolobus* spp.," J. Bacteriology, 2006, 188:8551-8559.

Anton et al., Polyamides, Fibers, Encyclopedia of Polymer Science and Engineering, 2001, 11:409-445.

Azuma et al., "Naphthalene—a constituent of Magnolia flowers," Phytochemistry, 1996, 42:999-1004.

"Brenda—The comprehensive Enzyme Information System," Jul. 2011, retrieved on Sep. 19, 2014, http://web.archive.org/web/20111009205602/http://www.brenda-enzymes.org/, 1 page.

Bennett et al., "Purification and properties of ξ-caprolactone hydrolases from *Acinetobacter* NCIB 9871 and *Nocardia globevula* CL1," Journal of General Microbiology, 1988 134: 161-168.

Bernstein et al., "Transfer of the high-GC cyclohexane carboxylate degradation pathway from *Rhodopseudomonas palustris* to *Escherichia coli* for production of biotin," Metabolic Engineering, May 2008, 10(3-4):131-140.

Berthold et al., "Structure of the branched-chain keto acid decarboxylase (KdcA) from *Lactococcus lactis* provides insights into the structural basis for the chemoselective and enantioselective carboligation reaction," Acta Crystallographica Sec. D, 2007, D63:1217-1224.

Binieda et al., "Purification, characterization, DNA Sequence and cloning of a pimeloyl-CoA synthetase from *Pseudomonas medocin* 35," Biochem J., 1999, 340:793-801.

Bordes et al., "Isolation of a thermostable variant of Lip2 lipase from *Yarrowia lipolytica* by directed evolution and deeper insight into the denaturation mechanisms," Journal of Biotechnology, 2011, 156: 117-124.

Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.

Boylan et al., "Functional identification of the fatty acid reductase components encoded in the luminescence operon of *Vibrio fischeri*," Journal of Bacteriology, 1985, 163(3):1186-1190.

Boylan et al., "Lux C, D and E genes of the *Vibrio fischeri* luminescence operon code for the reductase, transferase, and synthetase enzymes involved in aldehyde biosynthesis," Photochemistry and photobiology, 1989, 49:681-688.

Bramer et al., "The methylcitric acid pathway in *Ralstonia eutropha*: new genes identified involved in propionate metabolism," Microbiology 2001, 147:2203-2214.

Breithaupt et al., "Crystal structure of 12-oxophytodienoate reductase 3 from tomato: self-inhibition by dimerization," Proc Natl. Acad Sci. USA, 2006, 103:14337-14342.

Brzostowicz et al., "mRNA differential display in a microbial enrichment culture: simultaneous identification of three cyclohexanonemonooxygenases from three species," Applied and Environmental Microbiology, 2003, 69: 334-342.

Brzostowicz et al., "Identification of two gene clusters involved in cyclohexanone oxidation in *Brevibacterium epidermidis* strain HCU," Applied and Microbiological Biotechnology, 2002, 58:781-789.

Buckel et al., "Glutaconate CoA-transferase from *Acidaminococcus fermentans*," Eur J. Biochem, 1981, 118:315-321.

Buhler et al., "Occurrence and the possible physiological role of 2-enoate reductases," FEBS Letters, 1980, 109:244-246.

Bult et al., "Complete genome sequence of the methanogenicarchaeon, *Methanococcus jannaschii*," Science, 1996, 273: 1058-1073.

Bunik et al., "Kinetic properties of the 2-oxoglutarate dehydrogenase complex from *Azotobacter vinelandii* evidence for the formation of a precatalytic complex with 2-oxoglutarate," Eur J Biochem., 267(12):3583-3591, Jun. 2000.

Chayabutra and Ju, "Degradation of n-hexadecane and its metabolites by *Pseudomonas aeruginosa* under microaerobic and anaerobic denitrifying conditions," Appl Environ Microbiol., 66(2):493-498, Feb. 2000.

Cheesbrough and Kolattukudy, "Alkane biosynthesis by decarbonylation of aldehydes catalyzed by a particulate preparation from *Pisum sativum*," PNAS USA, 1984, 81(21):6613-7.

Chen et al., "Termites fumigate their nests with naphthalene," Nature, 1998, 392:558-559.

Cheng et al., "Genetic Analysis of a Gene Cluster for Cyclohexanol Oxidation in *Acinetobacter* sp. Strain SE19 by in Vitro Transposition," Journal of Bacteriology, 2000, 182(17):4744-4751.

Coon, "Omega oxygenases: nonheme-iron enzymes and P450 cytochromes," Biochemical & Biophysical Research Communications, 2005,338:378-385.

Cronan and Lin, "Synthesis of the $\alpha,\omega$-dicarboxylic acid precursor of biotin by the canonical fatty acid biosynthetic pathway," Current Opinion in Chem Biol., 2011, 15:407-413.

Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.

Cryle et al., "Carbon-carbon bond cleavage by cytochrome P450BioI (CYP107H1) E1," Chemical Communications, Jan. 2004, 86-87.

Cryle, "Selectivity in a barren landscape: the P450BioI-ACP complex," Biochemical Society Transactions, Aug. 2010, 38(4):934-939.

Da Silva et al., "Glycerol: A promising and abundant carbon source for industrial microbiology," Biotechnology Advances, 2009, 27:30-39.

Daisy et al., "Naphthalene, an insect repellent, is produced by *Muscodor vitigenus*, a novel endophytic fungus," Microbiology, 2002, 148:3737-3741.

Dalby, "Optimizing enzyme function by directed evolution," Current Opinion in Structural Biology, 2003, 13, 500-505.

Day et al., "Partial purification and properties of acyl-CoA reductase from *Clostridum butyricum*," Archives of Biochemistry and Biophysics, 1978, 190(1):322-331.

Deana et al., "Substrate specificity of a dicarboxyl-CoA: Dicarboxylic acid coenzyme . A transferase from rat liver mitochondria," Biochem Int., 1992, 26:767-773.

Dellomonaco et al., "Engineered reversal of the [beta]-oxidation cycle for the synthesis of fuels and chemicals," Nature, Jan. 2011, 476(7360):355-359.

Deshmukh and Mungre, "Purification and properties of 2-aminoadipate: 2-oxoglutarate aminotransferase from bovine kidney," Biochem J, 1989, 261(3):761-768.

Doan et al., "Functional expression of five Arabidopsis fatty acyl-CoA reductase genes in *Escherichia coli*," J. Plant Physiology, 2009, 166:787-796.

Dobritzsch et al., "High resolution crystal structure of pyruvate decarboxylase from *Zymomonas mobilis*. Implications for substrate activation in pyruvate decarboxylases," J. Biol. Chem., 1998, 273:20196-20204.

Donoghue and Trudgill, "The Metabolism of Cyclohexanol by *Acinetobacter* NCIB9871," Eur J Bochem., 1975, 60:1-7.

Drevland et al., "Enzymology and Evolution of the Pyruvate Pathway to 2-Oxobutyrate in *Methanocaldococcus jannaschii*," J. Bacteriol., Apr. 2007, 189(12):4391-4400.

Drevland et al., "Methanogen homoaconitase catalyzes both hydrolyase reactions in coenzyme B biosynthesis," J Biol Chem., Oct. 2008, 283: 28888-28896.

Egmond et al., "*Fusarium solani* pisi cutinase," Biochimie, Nov. 2000, 82(11):1015-1021.

Elshahed et al., "Benzoate Fermentation by the Anaerobic bacterium *Syntrophus aciditrophicus* in the Absence of Hydrogen-Using Microorganisms," Applied and Environ Microbiology, 2001, 67(12):5520-5525.

Elshahed et al., "Metabolism of Benzoate, Cyclohex-1-ene Carboxylate, and Cyclohexane Carboxylate by *Syntrophus aciditrophicus* Strain SB in Syntrophic Association with H2-Using Microorganisms," Applied and Environ. Microbiol., Apr. 2001, 67(4):1728-1738.

(56) References Cited

OTHER PUBLICATIONS

Eurich et al., "Cloning and characterization of three fatty alcohol oxidase genes from *Candida tropicalis* strain ATCC 20336," Applied & Environmental Microbiology, 2004, 70(8): 4872-4879.
Ferreira et al. "A member of the sugar transporter family, St11p is the glycerol/H= symporter in *Saccharomyces cerevisiae*," Molecular Biology of the Cell, American Society for Cell Biology, Apr. 1, 2005, 16(4):2068-2076.
Fickers et al., "Carbon and nitrogen sources modulate lipase production in the yeast *Yarrowia lipolytica*," Journal of Applied Microbiology, 2004, 96:742-9.
Fickers et al., "The lipases from *Yarrowia lipolytica*: Genetics, production, regulation, biochemical characterization and biotechnological applications," Biotechnology Advances, 2011, 29: 632-644.
Fuchs et al., "Microbial degradation of aromatic compounds—from one strategy to four," Nat Rev Microbiol., Oct. 3, 2011;9(11):803-816, Oct. 2011.
Gallus and Schink, "Anaerobic degradation of pimelate by newly isolated denitrifying bacteria," Microbiology, 1994, 140:409-416.
Gasmi et al., "A molecular approach to optimize hIFN α2b expression and secretion in *Yarrowia lipolytica*," Appl Microbiol Biotechnol, 2011, 89:109-119.
GenBank Accession No. AAA24664.1, Mar. 25, 1993, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct 23, 2009, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
GenBank Accession No. AAF02538.1, Oct. 20, 1999, 2 pages.
Genbank Accession No. AAK73167.2, retrieved May 19, 2014, 1 page.
Genbank Accession No. AAN37290.1, retrieved May 19, 2014, 1 page.
GenBank Accession No. AAO77182, Mar. 28, 2003, 1 page.
GenBank Accession No. AAS11092.1, Mar. 5, 2010, 1 page.
GenBank Accession No. AAS43086.1, dated Nov. 2011, 1 page.
Genbank Accession No. AAT43726, retrieved May 19, 2014, 1 page.
GenBank Accession No. AAW66853.1, Feb. 12, 2005, 1 page.
GenBank Accession No. AB005294, Feb. 2000, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
Genbank Accession No. ABE47159.1, Jan. 28, 2014, 2 pages.
Genbank Accession No. ABJ63754.1, dated Mar. 2010, 1 page.
Genbank Accession No. ABK75684.1, Jan. 31, 2014, 2 pages.
Genbank Accession No. ACJ06772.1, Dec. 4, 2009, 1 page.
GenBank Accession No. ADK19581.1, Sep. 20, 2010, 2 pages.
GenBank Accession No. AJ012480.1, Apr. 2005, 2 pages.
GenBank Accession No. AY143338, Apr. 2003, 5 pages.
Genbank Accession No. AY495697, Mar. 2004, 3 pages.
Genbank Accession No. BAB91331.1, retrieved May 19, 2014, 1 page.
Genbank Accession No. BAC06606, Aug. 1, 2002, 1 page.
GenBank Accession No. BAD69624, Sep. 2005, 1 page.
GenBank Accession No. BAF92773, Nov. 27, 2007, 1 page.
Genbank Accession No. BAF94304.1, retrieved May 19, 2014, 1 page.
Genbank Accession No. CAA44858.1, Apr. 28, 1992, 1 page.
Genbank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 page.
GenBank Accession No. CAE26094.1, Apr. 17, 2005, 2 pages.
GenBank Accession No. CAE26097.1, Apr. 17, 2005, 2 pages.
Genbank Accession No. CAH04396.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. NM_001246944, Dec. 2011, 2 pages.
GenBank Accession No. NM_001247852, Dec. 2011, 2 pages.
GenBank Accession No. NM_133240, Feb. 25, 2002, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus Sphaericus* genes controlling the bioconversion of pimlate into dethiobiotin," Gene, 1990, 87:63-70.
Gocke et al., "Comparative characterization of ThPP-dependent decarboxylases," J. Mol. Cat. B: Enzymatic, 2009, 61:30-35.
Gonzalez-Lopez, "Genetic control of extracellular protease synthesis in the yeast *Yarrowia lipolytica*," Genetics, 2002, 160: 417-427.
Graupner et al., "Identification of the gene encoding sulfopyruvate decarboxylase, an enzyme involved in biosynthesis of coenzyme M," J Bacteriol., 2000, 182: 4862-4867.
Hall, "The Contribution of Horizontal Gene Transfer to the Evolution of Fugi," Duke University Libraries, May 10, 2007, 163 pages.
Hall, "Asymmetric bioreduction of activated alkenes using cloned 12-oxophytodienoate reductase isoenzymes OPR-1 and OPR-3 from *Lycopersicon esculentum* (tomato): a striking change of stereoselectivity," Agnew Chem Int. Ed., 2007, 46:3934-3937.
Han et al., "Oxaloacetate hydrolase, the C-C bond lyase of oxalate secreting fungi," J. Biol. Chem. 2007, 282:9581-9590.
Harrison and Harwood, "The pimFABCDE operon from *Phodopseudomonas palustris* mediates dicarboxylic acid degradation and participates in anaerobic benzoate degradation," Microbiology, 2005, 151:727-736.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from *Bacillus subtilis*," J Biol Chem., 275(51):40128-40133, Dec. 22, 2000.
Hess et al., "Extremely thermostable esterases from the thermoacidophilic euryarchaeon *Picrophilus torridus*," Extremophiles, 2008, 12:351-364.

(56) References Cited

OTHER PUBLICATIONS

Hoffmeister et al., "Mitochondrial trans-2-enoyl-CoA reductase of wax ester fermentation from *Euglena gracilis* defines a new family of enzymes involved in lipid synthesis," J Biol Chem., 280(6):4329-4338. Epub Nov. 29, 2004.

Hofvander et al., "A prokaryotic acyl-CoA reductase performing reduction of fatty acyl-CoA to fatty alcohol," FEBS Letters, 2001, 585:3538-3543.

Holden et al., "Chorismate lyase: kinetics and engineering for stability," Biochim Biophys Acta., Jan. 31, 2002, 1594(1):160-167.

Hooks et al., "Long-chain acyl-CoA oxidases of *Arabidopsis*," Plant J., 1999, 20:1-13.

Hotta et al., "Extremely Stable and Versatile Carboxylesterase from a Hyperthermophilic Archaeon," Applied and Environmental Microbiology, 2002, 68(8):3925-3931.

Howell et al., "Alpha-keto acid chain elongation reactions involved in the biosynthesis of coenzyme B (7-mercaptoheptanoyl threonine phosphate) in methanogenic Archaea," Biochemistry, 1989, 37: 10108-10117.

Howell et al., "Identification of enzymes homologous to isocitrate dehydrogenase that are involved in coenzyme B and leucine biosynthesis in methanoarchaea," J Bacteriol., Sep. 2000, 182: 5013-5016.

Hugler et al., "Malonyl-coenzyme A reductase from *Chloroflexus aurantiacus*, a key enzyme of the 3-hydroxypropionate cycle for autotrophic CO(2) fixation," J. Bacteriology, 2002, 184:2404-2410.

Hunt et al., "Characterization of an acyl-CoA thioesterase that functions as a major regulator of peroxisomal lipid metabolism," J. Biol Chem, 2002, 277:1128-1138.

International Preliminary Report on Patentability for International Application No. PCT/US 2012/069934, mailed Jun. 17, 2014, 15 pages.

International Preliminary Report on Patentability in International Application No. PCT/US 2012/042777, mailed Jan. 10, 2013, 22 pages.

International Preliminary Report on Patentability in International Application No. PCT/US 2012/044984, mailed Jan. 28, 2014, 11 pages.

International Search Report and Written Opinion for International Application No. PCT/US 2012/069934, mailed Jan. 17, 2014, 21 pages.

International Search Report and Written Opinion in International Application No. PCT/US 2012/042747, mailed Jan. 14, 2013, 19 pages.

International Search Report and Written Opinion in International Application No. PCT/US 2012/042777, mailed Sep. 11, 2012, 9 pages.

International Search Report and Written Opinion in International Application No. PCT/US 2012/044984, mailed Dec. 17, 2013, 17 pages.

International Search Report and Written Opinion in International Application No. PCT/US 2012/071472, mailed Dec. 17, 2013, 17 pages.

International Search Report and Written Opinion in International Application No. PCT/US2013/075058, mailed Sep. 15, 2014, 17 pages.

International Search Report and Written Opinion in International Application No. PCT/US2013/075087, mailed Aug. 4, 2014, 18 pages.

International Search Report and Written Opinion in International Application No. PCT/US2013/077411, mailed Sep. 24, 2014, 18 pages.

International Search Report and Written Opinion in International Application No. PCT/US2013/077413, mailed Jul. 22, 2014, 20 pages.

International Search Report and Written Opinion in International Application No. PCT/US2013/077419, mailed Jun. 16, 2014, 19 pages.

International Search Report and Written Opinion in International Application No. PCT/US2013/077420, mailed Jul. 21, 2014, 21 pages.

International Search Report and Written Opinion in International Application No. PCT/US2013/077423, mailed Jul. 21, 2014, 22 pages.

International Search Report and Written Opinion in International Application No. PCT/US2013/077445, mailed Sep. 15, 2014, 17 pages.

Invitation to Pay Additional Fees in International Application No. PCT/US2013/075058, mailed Jul. 7, 2014, 7 pages.

Invitation to Pay Additional Fees in International Application No. PCT/US2013/07745, mailed Jul. 7, 2014, 9 pages.

Invitation to Pay Fees in International Application No. PCT/US2013/075087, mailed May 16, 2014, 9 pages.

Invitation to Pay Fees in International Application No. PCT/US2013/077411, mailed Jul. 16, 2014, 9 pages.

Invitation to Pay Fees in International Application No. PCT/US2013/077413, mailed May 12, 2014, 9 pages.

Invitation to Pay Fees in International Application No. PCT/US2013/077419, mailed Apr. 16, 2014, 9 pages.

Invitation to Pay Fees in International Application No. PCT/US2013/077420, mailed May 13, 2014, 9 pages.

Invitation to Pay Fees in International Application No. PCT/US2013/077423, mailed May 13, 2014, 10 pages.

Invitation to Pay Fees in International Application No. PCT/US2013/077430, mailed Aug. 25, 2014, 9 pages.

Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbilogy, 2002, 68:1192-1195.

Ishikawa et al., "The pathway via D-galacturonate/L-galactonate is significant for ascorbate biosynthesis in *Euglena gracilis*: identification and functional characterization of aldonolactonase," Journal of Biologiocal Chemistry, 2008, 283:31133-31141.

Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.

Izumi et al., "Structure and Mechanism of HpcG, a Hydratase in the Homoprotocatechuate Degradation Pathway of *Escherichia coli*," J. Mol. Biol., 2007, 370:899-911.

Izumi et al., "The pimeloyl-CoA synthetase responsible for the first step in biotin biosynthesis by microorganisms," Agr. Biol. Chem., 1974, 38:2257-2262.

Jacob et al., "Glutaconate CoA-transferase from *Acidamiococcus fermentans*: the crystal structure reveals homology with other CoA-transferases," Structure, 1997, 5:415-426.

Jeyakanthan et al., "Substrate specificity determinants of the methanogen homoaconitase enzyme: structure and function of the small subunit," Biochemistry, 2010, 49:2687-2696.

Jing et al., "Phylogenetic and experimental characterization of an acyl-ACP thioesterase family reveals significant diversity in enzymatic specificity and activity," BMC Biochemistry, 2011, 12:44, 16 pages.

Joon-Young et al., "Production of 1,2-Propanediol from Glycerol in *Saccharomyces cerevisiae*," J. Microbiology and Biotechnology, May 19, 2011, 21(8):846-853.

Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.

Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.

Kikuchi et al., "Characterization of a second lysine decarboxylase isolated from *Escherichia coli*," J Bacteriol, 1997, 179(14): 4486-4489.

Kim et al., "Cloning and characterization of a cyclohexanone monooxygenase gene from *Arthrobacter* sp. L661," Biotechnology Bioprocess Engineering, 2008, 13:40-47.

(56) References Cited

OTHER PUBLICATIONS

Kitzing et al., "The 1.3 Å crystal structure of the flavoprotein YqjM reveals a novel class of Old Yellow Enzymes," J. Biol. Chem., 2005, 280:27904-27913.
Koch et al., "Products of Enzymatic Reduction of Benzoyl-CoA, A Key Reaction in Anaerobic Aromatic Metabolism," Eur. J. Biochemistry, Jan. 1993, 211(3):649-661.
Kockelkorn and Fuchs, "Malonic semialdehyde reductase, succinic semialdehyde reductase, and succinyl-coenzyme A reductase from *Metallosphaera sedula*: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Kung et al., "Cyclohexane carboxyl-coenzyme A (CoA) and cyclohex-l-ene-1-carboxyl-CoA dehydrogenases, two enzymes involved in the fermentation of benzoate and crotonate in *Syntrophus aciditrophicus*," J Bacteriol., 195(14):3193-3200, Epub May 10, 2013.
Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.
Le Dall et al., "Multiple-copy integration in the yeast *Yarrowia lipolytica*," Current Genetics, 1994 26:38-44.
Lee and Meighen, "Cysteine-286 as the site of acylation of the LUX-specific fatty acyl-CoA reductase," Biochim Biophys Acta, 1997, 1338:215-222.
Lin and Cronan, "Closing in on complete pathways of biotin biosynthesis," Molecular Biosystems, 2011, 7:1811-1821.
Lin et al., "Biotin Sythesis Begins by Hijacking the Fatty Acid Synthetic Pathway," Nature Chem Biol., Sep. 2010, 6:682-688.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin, "Biotin Synthesis in *Escherichia coli*," PhD Dissertation, University of Illinois at Urbana-Champaign, 2012, 140 pages.
Liu et al., "Two novel metal-independent long-chain alkyl alcohol dehydrogenases from *Geobacillus* thermodenitrificans NG80-2," Microbiology, 2009, 155:2078-2085.
Luo et al., "Production of 3-hydroxypropionic acid through propionaldehyde dehydrogenase PduP mediated biosynthetic pathway in *Klebsiella pneumoniae*," Bioresource Technology, 2012, 103:1-6.
Mack and Buckel, "Conversion of glutaconate CoA-transferase from *Acidaminococcus fermentans* into an acyl-CoA hydrolase by site-directed mutagenesis," FEBS Letters, 1997, 405:209-212.
Maeda et al., "Purification and characterization of a biodegradable plastic-degrading enzyme from *Aspergillus oryzae*," Applied and Environmental Biotechnology, 2005, 67: 778-788.
Mahadik et al., "Production of acidic lipase by *Aspergillus niger* in solid state fermentation," Process Biochemistry, 2002, 38: 715-721.
Martinez et al., "*Fusarium solani* cutinase is a lipolytic enzyme with a catalytic serine accessible to solvent," Nature, 1992, 356:615-618.
Mawal and Deshmukh, "Alpha-aminoadipate and kynurenine aminotransferase activities from rat kidney. Evidence for separate identity," J. Biol Chem, 1991, 266(4):2573-2575.
McAndrew et al., "Structural basis for substrate fatty acyl chain specificity: crystal structure of human very-long-chain acyl-CoA dehydrogenase," J. Biol. Chem., 2008, 283:9435-9443.
Mhetras et al., "Purification and characterization of acidic lipase from *Aspergillus niger* NCIM 1207," Bioresource Technology, 2009, 100: 1486-1490.
Millar et al., "CUT1, an *Arabidopsis* Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.

Miyazaki et al., "Alpha-Aminoadipate aminotransferase from an extremely thermophilic bacterium, *Thermus thermophilus*," Microbiology, 2004, 150(7): 2327-2334.
Mouttaki et al., "Cyclohexane Carboxylate and Benzoate Formation from Crotonate in *Sytrophus aciditrophicus*," Applied and Environ Microbiology, Feb. 2007, 73(3):930-938.
Murphy et al., "*Fusarium* polycaprolactone depolymerase is cutinase," Appl. Environm. Microbiol., 1996, 62:456-460.
Nicol et al., "Bioconversion of crude glycerol by fungi," Applied Microbiology and Biotechnology, Feb. 10, 2012, 93(5):1865-1875.
Nieder and Shapiro, "Physiological function of the *Pseudomonas putida* PpG6 (*Pseudomonas oleovorans*) alkane hydroxylase: monoterminal oxidation of alkanes and fatty acids," J. Bacteriol., 1975, 122(1):93-98.
Onakunle et al., "The formation and substrate specificity of bacterial lactonases capable of enantioselective resolution of racemic lactones," Enzyme and Microbial Technology, 1997, 21: 245-251.
Oppenheim and Dickerson, "Adipic Acid," Kirk-Othmer Encyclopedia of Chemical Technology, 2003.
Ouchi et al., "Dual roles of a conserved pair, Arg23 and Ser20, in recognition of multiple substrates in alpha-aminoadipate aminotransferase from *Thermus thermophilus*," Biochem Biophys Res Commun, 2009, 388(1):21-27.
Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.
Pelletier and Harwood et al., "2-Hydroxycyclohexanecarboxyl coenzyme A dehydrogenase, an enzyme characteristic of the anaerobic benzoate degradation pathway used by *Rhodopseudomonas palustris*," J Bacteriol., 182(10):2753-2760, May 2000.
Peterson et al., "The Thermal Stability of the *Fusarium solani* pisi Cutinase as a Function of pH," BioMed Research International, 2001, 1.2:62-69.
Pignede et al., "Autocloning and Amplification of LIP2 in *Yarrowia lipolytica*,"Appl. Environ. Microbiol, 2000 66:3283-3289.
Pignede et al., "Characterization of an extracellular lipase encoded by LIP2 in *Yarrowia lipolytica*," Journal of Bacteriology, 2000, 182: 2802-2810.
Ploux et al., "Investigation of the first step of biotin biosynthesis in *Bacillus sphaericus*: Purification and characterization of the pimloyl-CoA synthase, and uptake of pimelate," Biochem J., 1992, 287:685-690.
Qian et al., "Metabolic engineering of *Escherichia coli* for the production of cadaverine: a five carbon diamine," Biotechnol Bioeng, 2011, 108(1):93-103.
Qiu et al., "Crystal structure and substrate specificity of the β-ketoacyl-acyl carrier protein synthase III (FabH) from *Staphylococcus aureus*," Protein Sci, 2005, 14(8):2087-2094.
Ray et al., "Cocrystal structures of diaminopimelate decarboxylase: mechanism, evolution, and inhibition of an antibiotic resistance accessory factor," Structure, 2002, 10(11):1499-1508.
Rea et al., "Structure and Mechanism of HpcH: A Metal Ion Dependent Class II Aldolase from the Homoprotocatechuate Degradation Pathway of *Escherichia coli*," J. Mol. Biol., 2007, 373:866-876.
Rohdich et al., "Enoate reductases of *Clostridia*. Cloning, sequencing, and expression," J. Biol. Chem., 2001, 276:5779-5787.
Roje, "Vitamin B biosynthesis in plants," Phytochemistry, 2007, 68:1904-1921.
Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.
Ryu et al., "A novel synthesis of .beta.-trichlorostannyl ketones from siloxycyclopropanes and their facile dehydrostannation affording 2-methylene ketones," JOC, 1986, 51:2389-2391.
Salcher and Lingens, "Regulation of phospho-2-keto-3-deoxyheptonate aldolase (DAHP synthase) and anthranilate synthase of *Pseudomonas aureofaciens*," J Gen Microbiol., 121(2):473-476, Dec. 1980.
Sambrook et al., Molecular Cloning—a Laboratory Manual, Cold Spring Harbor Laboratory Press, 2001.
Schirmer et al., "Microbial Biosynthesis of Alkanes," Science, 2010, 329:559-562.

(56) References Cited

OTHER PUBLICATIONS

Schwartz et al., "A proteomic view of the facultatively chemolithoautotrophic lifestyle of *Ralstonia eutropha* H16," Proteomics, 2009, 9:5132-5142.
Shapiro et al., "Remarkable Diversity in the Enzymes Catalyzing the Last Step in Synthesis of the Pimelate Moiety of Biotin," PLoSOne, Nov. 2012, 7(11):e49440, 11 pages.
Shikata et al., "A novel ADP-forming succinyl-CoA synthetase in *Thermococcus kodakaraensis* structurally related to the archaeal nucleoside diphosphate-forming acetyl-CoA synthetases," J. Biol. Chem, 2007, 282(37):26963-26970.
Siegert et al., "Exchanging the substrate specificities of pyruvate decarboxylase from *Zymomonas mobilis* and benzoylformate decarboxylase from *Pseudomonas putida*," Port. Eng. Des. Sel., 2005, 18:345-357.
Simon et al., "Chiral Compounds Synthesized by Biocatalytic Reductions [New Synthetic Methods (51)]," Angew Chem Ed Engl., 1985, 24:539-553.
Simon, "Properties and mechanistic aspects of newly found redox enzymes from anaerobes suitable for bioconversions on preparatory scale," Pure and Appl. Chem, 1992, 64:1181-1186.
Smith et al., "Complete genome sequence of *Methanobacterium thermoautotrophicum* deltaH: functional analysis and comparative genomics," J Bacteriol., 1997, 179: 7135-7155.
Smith et al., "Structural analysis of ligand binding and catalysis in chorismate lyase," Archives of Biochemistry and Biophysics, Jan. 2006, 445(1):72-80.
Stok et al., "Expression, Purification, and Characterization of BioI• A Carbon-Carbon Bond Cleaving Cytochrome P450 Involved in Biotin Biosynthesis in *Bacillus subtilis*," Archives of Biochemistry and Biophysics, Dec. 2000, 384(2):351-360.
Strassner et al., "A homolog of old yellow enzyme in tomato. Spectral properties and substrate specificity of the recombinant protein," J. Biol. Chem. 1999, 274:35067-35073.
Stueckler, "Stereocomplementary bioreduction of alpha,beta-unsaturated dicarboxylic acids and dimethyl esters using enoate reductases: enzyme- and substrate-based stereocontrol," Org. Left., 2007, 9:5409-5411.
Suzuki et al., "Antimicrobial Activity of Meropenem Against Main Bacterial Species Isolated from Patient Blood in 2006," J. Antibiot., 2007, 60(6):380-387.
Tomita et al., "Mechanism for multiple-substrates recognition of alpha-aminoadipate aminotransferase from *Thermus thermophilus*," Proteins, 2009, 75(2):348-359.
Tseng et al., "Biosynthesis of chiral 3-hydroxyvalerate from single propionate-unrelated carbon sources in metabolically engineered *E. coli*," Microbial Cell Factories, 2010, 9:96.
US Non-Final Office Action in U.S. Appl. No. 13/524,883, mailed Nov. 29, 2013, 13 pages.
US Notice of Allowance in U.S. Appl. No. 13/524,883, mailed May 29, 2014, 7 pages.
Vamecq et al., "The microsomal dicarboxylyl-CoA synthetase," Biochem J., 1985, 230:683-693.
Vioque et al., Resolution and purification of an aldehyde-generating and an alcohol-generating fatty-acyl-CoA reductase from Pea leaves (*Pisum sativum* L), Archives of Biochemistry and Biophysics, 1997, 340(1):64-72.
Wahlen et al., "Purification, characterization and potential bacterial wax production role of an NADPH-dependent fatty aldehyde reductase from *Marinobacter aquaeolei* VT8," Appl. Environ Microbiol, 2009, 75:2758-2764.
Wang and Kolattukudy, "Solubilization and purification of aldehyde-generation fatty acyl-CoA reductase from green alga *Botryococcus braunii*," FEBS Letters, 1995, 370:15-18.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia Coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of *Candida antarctica* lipase A," BMC Genomics, 2010, 11:123-130.
Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.
Wischgoll et al., "Structural basis for promoting and preventing decarboxylation in glutaryl-coenzyme, A dehydrogenases," Biochemistry, 2010, 49:5350-5357.
Xiong et al., "A bio-catalytic approach to aliphatic ketones," Sci Rep., 2:311, Epub Mar. 13, 2012.
Zhang et al., "Expanding metabolism for biosynthesis of non-natural alcohols," Proc Natl Acad Sci U S A., 105(52):20653-20658 Epub Dec. 8, 2008.
Aimin et al., "Nocardia sp. carboxylic acid reductase: cloning, expression, and characterization of a new aldehyde oxidoreductase family," Appl. Environ. Microbiol., 2004, 70:1874-1881.
Aloulou et al., "Purification and biochemical characterization of the LIP2 lipase from *Yarrowia lipolytica*," Biochim. Biophys. Acta, 2007, 1771:228-237.
Atsumi et al., "Acetolactate synthase from Bacillus subtilisserves as a 2-ketoisovalerate decarboxylase from isobutanol synthesis in Escherichi coli," Applied and Environ. Microbiol., 2009, 75(19):6306-6311.
Bergler et al., "Protein EnvM is the NADH-dependent enoyl-ACP reductase (FabI) of Escherichia coli," J. Bio Chem, 1993, 269(8):5493-5496.
Chinese Office Action in Chinese Application No. 2012800401576, mailed Oct. 17, 2014, 7 pages (with English Translation).
Eikmanns and Buckel, "Properties of 5-hydroxyvalerate CoA-transferase from Clostridium aminovalericum," Biol. Chem, 1990, 371:1077-1082.
Fonknechten et al., "Clostridium sticklandii, a specialist in amino acid degradation: revisiting its metabolism through its genome sequence," BMC Genomics, 2010, 11:1-12.
GenBank Accession No. AAA23536, Apr. 26, 1993, 1 page.
Genbank Accession No. AAA92347.1, Mar. 15, 1996, 1 page.
GenBank Accession No. AAB99100, Aug. 27, 1996, 2 pages.
GenBank Accession No. AE000666.1, Jan. 5, 2006, 309 pages.
GenBank Accession No. D87518, Jul. 31, 1997, 2 pages.
GenBank Accession No. HQ418483.1, Apr. 4, 2011, 2 pages.
GenBank Accession No. JA114119.1, Apr. 19, 2011, 1 page.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.

(56) References Cited

OTHER PUBLICATIONS

Horning et al., "α-Ketoglutaric Acid," Organic Syntheses, 1955, 3: 510-512.

International Search Report and Written Opinion in International Application No. PCT/US2014/052950, mailed Dec. 3, 2014, 15 pages.

International Search Report and Written Opinion in International Application No. PCT/US2013/077430, mailed Nov. 10, 2014, 23 pages.

Invitation to Pay Additional Fees in International Application No. PCT/US2014/053222, mailed Dec. 15, 2014, 8 pages.

Klatte et al., "Redox self-sufficient whole cell biotransformation for amination of alcohols," Bioorg & Medicinal Chem, May 2014, 22: 5578-5585.

Lea et al., "Long-chain acyl-CoA dehydrogenase is a key enzyme in the mitochondrial B-oxidation of unsaturated fatty acids," Biochmica et Biophysica Acta, 2000, 1485: 121-128.

Mutti et al., "Amination of ketones by employing two new (S)-selective w-transaminases and the His-tagged w-TA from Vibrio fluvialis," Eur. J. Org. Chem, 2012, 1003-1007 (Abstract).

Prabhu et al., "Lactate and Acrylate Metabolism by Megasphaera elsdenii under Batch and Steady-State Conditions," Applied and Environ. Microbiology, Sep. 2012, 78(24): 8564-8570.

Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.

Rizzarelli et al., "Evidence for Selective Hydrolysis of Aliphatic Copolyesters Induced by Lipase Catalysis," Biomacromolecules, 2004, 5:433-444.

Uniprot Accession No. I5YEB8, Sep. 5, 2012, 1 page.

US Non-Final Office Action in U.S. Appl. No. 13/715,826, mailed Jan. 30, 2015, 24 pages.

US Notice of Allowance in U.S. Appl. No. 14/106,124, mailed Dec. 24, 2014, 31 pages.

Vyazmensky et al., "Isolation and Characterization of Subunits of Acetohydroxy Acid Synthase Isozyme III and Reconstruction of the Holoenzyme," Biochemistry, 1996, 35:10339-10346.

Zhao et al., "Prediction and characterization of enzymatic activities guided by sequence similarity and genome neighborhood networks," E-Life, Jun. 2014, 3: 1-32.

\* cited by examiner

METHODS OF PRODUCING 6-CARBON CHEMICALS VIA COA-DEPENDENT CARBON CHAIN ELONGATION ASSOCIATED WITH CARBON STORAGE

CROSS-REFERENCE TO RELATED APPLICATIONS

This application claims priority to U.S. Application Ser. No. 61/576,401, filed Dec. 16, 2011. The disclosure of the application is incorporated by reference in its entirety.

TECHNICAL FIELD

This invention relates to methods for biosynthesizing adipic acid, 6-aminohexanoic acid, hexamethylenediamine, caprolactam, and 1,6-hexanediol using one or more isolated enzymes such as β-ketothiolases, dehydrogenases, reductases, hydratases, monooxygenases, ω-hydroxylases and transaminases or using recombinant host cells expressing one or more such enzymes.

BACKGROUND

Nylons are polyamides that are generally synthesized by the condensation polymerisation of a diamine with a dicarboxylic acid. Similarly, nylons may be produced by the condensation polymerisation of lactams. A ubiquitous nylon is nylon 6,6, which is produced by reaction of hexamethylenediamine (HMD) and adipic acid. Nylon 6 is produced by a ring opening polymerisation of caprolactam. Therefore, adipic acid, hexamethylenediamine and caprolactam are important intermediates in the production of nylons (Anton & Baird, Polyamides Fibers, Encyclopedia of Polymer Science and Technology, 2001).

Industrially, adipic acid and caprolactam are produced via air oxidation of cyclohexane. The air oxidation of cyclohexane produces, in a series of steps, a mixture of cyclohexanone (K) and cyclohexanol (A), designated as KA oil. Nitric acid oxidation of KA oil produces adipic acid (Musser, Adipic acid, Ullmann's Encyclopedia of Industrial Chemistry, 2000). Caprolactam is produced from cyclohexanone via its oxime and subsequent acid rearrangement (Fuchs, Kieczka and Moran, Caprolactam, Ullmann's Encyclopedia of Industrial Chemistry, 2000)

Industrially, hexamethylenediamine (HMD) is produced by hydrocyanation of C6 building block to adiponitrile, followed by hydrogenation to HMD (Herzog and Smiley, Hexamethylenediamine, Ullmann's Encyclopedia of Industrial Chemistry, 2012).

Given a reliance on petrochemical feedstocks; biotechnology offers an alternative approach via biocatalysis. Biocatalysis is the use of biological catalysts, such as enzymes, to perform biochemical transformations of organic compounds. Both bioderived feedstocks and petrochemical feedstocks are viable starting materils for the biocatalysis processes.

Accordingly, against this background, it is clear that there is a need for sustainable methods for producing adipic acid, caprolactam, 6-aminohexanoic acid, hexamethylenediamine and 1,6-hexanediol (hereafter "C6 building blocks") wherein the methods are biocatalyst based (Jang et al., Biotechnology & Bioengineering, 2012, 109(10), 2437-2459).

However, no wild-type prokaryote or eukaryote naturally overproduces or excretes C6 building blocks to the extracellular environment. Nevertheless, the metabolism of adipic acid and caprolactam has been reported (Ramsay et al., Appl. Environ. Microbiol., 1986, 52(1), 152-156; and Kulkarni and Kanekar, Current Microbiology, 1998, 37, 191-194).

The dicarboxylic acid, adipic acid, is converted efficiently as a carbon source by a number of bacteria and yeasts via β-oxidation into central metabolites. β-oxidation of adipate to 3-oxoadipate facilitates further catabolism via, for example, the ortho-cleavage pathway associated with aromatic substrate degradation. The catabolism of 3-oxoadipyl-CoA to acetyl-CoA and succinyl-CoA by several bacteria and fungi has been characterised comprehensively (Harwood and Parales, Annual Review of Microbiology, 1996, 50, 553-590). Both adipate and 6-aminohexanoate are intermediates in the catabolism of caprolactam, finally degraded via 3-oxoadipyl-CoA to central metabolites.

Potential metabolic pathways have been suggested for producing adipic acid from biomass-sugar: (1) biochemically from glucose to cis,cis muconic acid via the ortho-cleavage aromatic degradation pathway, followed by chemical catalysis to adipic acid; (2) a reversible adipic acid degradation pathway via the condensation of succinyl-CoA and acetyl-CoA and (3) combining β-oxidation, a fatty acid synthase and ω-oxidation. However, no information using these strategies has been reported (Jang et al., Biotechnology & Bioengineering, 2012, 109(10), 2437-2459).

The optimality principle states that microorganisms regulate their biochemical networks to support maximum biomass growth. Beyond the need for expressing heterologous pathways in a host organism, directing carbon flux towards C6 building blocks that serve as carbon sources rather than as biomass growth constituents, contradicts the optimality principle. For example, transferring the 1-butanol pathway from *Clostridium* species into other production strains has often fallen short by an order of magnitude compared to the production performance of native producers (Shen et al., Appl. Environ. Microbiol., 2011, 77(9), 2905-2915).

The efficient synthesis of the six carbon aliphatic backbone precursor is a key consideration in synthesizing C6 building blocks prior to forming terminal functional groups, such as carboxyl, amine or hydroxyl groups, on the C6 aliphatic backbone.

SUMMARY

This document is based at least in part on the discovery that it is possible to construct biochemical pathways for producing a six carbon chain aliphatic backbone precursor, in which two functional groups, e.g., carboxyl, amine or hydroxyl, can be formed, leading to the synthesis of one or more of adipic acid, 6-aminohexanoic acid, hexamethylenediamine, caprolactam, and 1,6-hexanediol (hereafter "C6 building blocks"). These pathways, metabolic engineering, and cultivation strategies described herein rely on CoA-dependent elongation enzymes or homologs thereof associated with the carbon storage pathways from polyhydroxyalkanoate accumulating bacteria such as *Cupriavidus necator*.

In the face of the optimality principle, it surprisingly has been discovered that appropriate non-natural pathways, feedstocks, host microorganisms, attenuation strategies to the host's biochemical network, and cultivation strategies may be combined to efficiently produce C6 building blocks.

In some embodiments, the C6 aliphatic backbone for conversion to a C6 building block can be formed from acetyl-CoA via two cycles of CoA-dependent carbon chain elongation using either NADH or NADPH dependent enzymes. See FIG. 1 and FIG. 2.

In some embodiments, the enzyme in the CoA-dependent carbon chain elongation pathway generating the C6 aliphatic backbone catalyzes irreversible enzymatic steps.

In some embodiments, the terminal carboxyl groups can be enzymatically formed using an acyl-CoA hydrolase, an aldehyde dehydrogenase, a 6-oxohexanoate dehydrogenase or a cytochrome P450/ω-hydroxylase. See FIG. 3 and FIG. 4.

In some embodiments, the terminal amine groups can be enzymatically formed using an ω-transaminase or a diamine transaminase. See FIG. 5 and FIG. 6.

In some embodiments, the terminal hydroxyl group can be enzymatically formed using a cytochrome P450, a monooxygenase, or an alcohol dehydrogenase. See FIG. 7 and FIG. 8.

In one aspect, this document features a method for biosynthesizing one or more products selected from the group consisting of adipic acid, 6-aminohexanoic acid, hexamethylenediamine, caprolactam, and 1,6-hexanediol. The method includes enzymatically synthesizing a six carbon chain aliphatic backbone (e.g., hexanoyl-CoA) and enzymatically forming, in one or more steps, two terminal functional groups selected from the group consisting of carboxyl, amine, and hydroxyl groups in the backbone to directly produce the product or producing the product in a subsequent step. The two terminal functional groups can be the same or can be different.

Hexanoyl-CoA can be enzymatically synthesized from acetyl-CoA via two cycles of CoA-dependent carbon chain elongation using either NADH or NADPH dependent enzymes. Hexanoyl-CoA can be formed by conversion of hex-2-enoyl-CoA by an enoyl-CoA reductase classified under EC 1.3.1.44, EC 1.3.1.38, or EC 1.3.1.8 such as the gene product of ter or tdter. Hex-2-enoyl-CoA can be formed by conversion of (S) 3-hydroxyhexanoyl-CoA by a trans-2-enoyl-CoA hydratase classified under EC 4.2.1.17 or by conversion of (R) 3-hydroxyhexanoyl-CoA by a trans-2-enoyl-CoA hydratase classified under EC 4.2.1.119. The trans-2-enoyl-CoA hydratase can be the gene product of crt. (S) 3-hydroxyhexanoyl-CoA can be formed by conversion of 3-oxohexanoyl-CoA by a 3-hydroxyacyl-CoA dehydrogenase classified under EC 1.1.1.35 such as the 3-hydroxyacyl-CoA dehydrogenase encoded by fadB. The 3-oxohexanoyl-CoA can be formed by conversion of butanoyl-CoA by an acetyl-CoA C-acyltransferase classified under EC 2.3.1.16 such as that encoded by bktB. Butanoyl-CoA can be formed by conversion of crotonyl-CoA by an enoyl-CoA reductase classified under EC 1.3.1.44, EC 1.3.1.38, or EC 1.3.1.8. Crotonyl-CoA can be formed by conversion of (S) 3-hydroxybutanoyl-CoA by a trans-2-enoyl-CoA hydratase classified under EC 4.2.1.17. The (S) 3-hydroxybutanoyl-CoA can be formed by conversion of acetoacetyl-CoA by a 3-hydroxybutyryl-CoA dehydrogenase classified under EC 1.1.1.157 such as a 3-hydroxybutyryl-CoA dehydrogenase is encoded by hbd. The acetoacetyl-CoA can be formed by conversion of acetyl-CoA by an acetyl-CoA C-acyltransferase classified under EC 2.3.1.9 such as that encoded by atoB or phaA. The acetoacetyl-CoA can be formed by conversion of malonyl-CoA by an acetoacetyl-CoA synthase classified under EC 2.3.1.194. The malonyl-CoA can be formed by conversion of acetyl-CoA by an acetyl-CoA carboxylase classified under EC 6.4.1.2. The trans-2-enoyl-CoA hydratase can be the gene product of phaJ.

The (R) 3-hydroxyhexanoyl-CoA can be formed by conversion of 3-oxohexanoyl-CoA by a 3-oxoacyl-CoA reductase classified under EC 1.1.1.100 such as that encoded by fabG. The crotonyl-CoA can be formed by conversion of (R) 3-hydroxybutanoyl-CoA by a trans-2-enoyl-CoA hydratase classified under EC 4.2.1.119. (R) 3-hydroxybutanoyl-CoA can be formed by conversion of acetoacetyl-CoA by an acetoacyl-CoA reductase classified under EC 1.1.1.36 such as that encoded by phaB.

In any of the methods described herein, the method can include producing hexanoate by forming a first terminal carboxyl group in hexanoyl CoA using an acyl-CoA hydrolase and an aldehyde dehydrogenase, or a thioesterase. The acyl-CoA hydrolase or thioesterase can be encoded by YciA, tesB or Acot13.

Hexanoate can be produced by forming a first terminal carboxyl group in hexanal by an aldehyde dehydrogenase classified under EC 1.2.1.4. Hexanal can be formed by conversion of hexanoyl-CoA by a butanal dehydrogenase classified under EC 1.2.1.57.

In any of the methods described herein, the methods can include converting hexanoate to adipic acid, 6-aminohexanoic acid, hexamethylenediamine, ε caprolactam or 1,6 hexanediol with one or more enzymatic conversions, wherein one of the enzymatic conversions introduces the second terminal functional group. The method can include converting hexanoate to 6-hydroxyhexanoate using a cytochrome P450/ω-hydroxylase such as from the family CYP153 such as CYP153A6. 6-hydroxyhexanoate can be converted to adipate semialdehyde using (i) an alcohol dehydrogenase such as encoded by YMR318C, (ii) a 6-hydroxyhexanoate dehydrogenase such as that encoded by ChnD, or (iii) a cytochrome P450/ω-hydroxylase.

In any of the methods described herein, adipic acid can be produced by forming the second terminal functional group in adipate semialdehyde using (i) an aldehyde dehydrogenase classified under EC 1.2.1.3, (ii) a 6-oxohexanoate dehydrogenase classified under EC 1.2.1.63 such as that encoded by ChnE or iii) a cytochrome P450/ω-hydroxylase.

In any of the methods described herein, 6-aminohexanoic acid can be produced by forming the second terminal functional group in adipate semialdehyde using an ω-transaminase classified under EC 2.61.18, EC 2.6.1.19 or EC 2.6.1.48.

In any of the methods described herein, caprolactam can be produced from 6-aminohexanoic acid using a lactamase classified under EC 3.5.2.-. The amide bond associated with caprolactam is the result of first having a terminal carboxyl group and terminal amine group to form the bond. 6-aminohexanoic acid can be converted to 6-aminohexanal using a carboxylate reductase classified under EC 1.2.99.6 such as that encoded by car alongside the gene product of npt, or GriC & GriD.

In any of the methods described herein, hexamethylenediamine can be produced by forming a second terminal functional group in 6-aminohexanal using a diamine transaminase classified under EC 2.6.1.29 or EC 2.6.1.82.

In any of the methods described herein, 1,6 hexandiol can be produced by forming the second terminal functional group in 6-hydroxyhexanal using an alcohol dehydrogenase classified under EC 1.1.1.-(1,2,21,184).

In some embodiments, the biological feedstock is, includes, or derives from, monosaccharides, disaccharides, lignocellulose, hemicellulose, cellulose, lignin such as levulinic acid and furfural, lignin, triglycerides such as glycerol and fatty acids, agricultural waste or municipal waste.

In some embodiments, the non-biological feedstock is or derives from natural gas, syngas, $CO_2/H_2$, methanol, ethanol, non-volatile residue (NVR) or a caustic wash waste stream from cyclohexane oxidation processes.

In some embodiments, the host microorganism is a prokaryote. For example, the prokaryote can be from the bacterial genus *Escherichia* such as *Escherichia coli*; from the bacterial genus *Clostridia* such as *Clostridium*

*ljungdahlii, Clostridium* autoethanogenum or *Clostridium kluyveri*; from the bacterial genus *Corynebacteria* such as *Corynebacterium glutamicum*; from the bacterial genus *Cupriavidus* such as *Cupriavidus necator* or *Cupriavidus metallidurans*; from the bacterial genus *Pseudomonas* such as *Pseudomonas fluorescens, Pseudomonas putida* or *Pseudomonas oleavorans*; from the bacterial genus *Delftia* such as *Delftia acidovorans*; from the bacterial genus *Bacillus* such as *Bacillus subtilis*; from the bacterial genus *Lactobacillus* such as *Lactobacillus delbrueckii*; or from the bacterial genus *Lactococcus* such as *Lactococcus lactis*. Such prokaryotes also can be sources of genes for constructing recombinant host cells described herein that are capable of producing C6 building blocks.

In some embodiments, the host microorganism is a eukaryote (e.g., a fungus such as a yeast). For example, the eukaryote can be from the fungal genus *Aspergillus* such as *Aspergillus niger*; from the yeast genus *Saccharomyces* such as *Saccharomyces cerevisiae*; from the yeast genus *Pichia* such as *Pichia pastoris*; from the yeast genus *Yarrowia* such as *Yarrowia lipolytica*; from the yeast genus *Issatchenkia* such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis*. Such eukaryotes also can be sources of genes for constructing recombinant host cells described herein that are capable of producing C6 building blocks.

In some embodiments, the host microorganism's tolerance to high concentrations of one or more C6 building blocks is improved through continuous cultivation in a selective environment.

In some embodiments, the host microorganism's biochemical network is attenuated or augmented to (1) ensure the intracellular availability of acetyl-CoA, (2) create an NADH or NADPH imbalance that may only be balanced via the formation of one or more C6 building blocks, (3) prevent degradation of central metabolites, central precursors leading to and including C6 building blocks and (4) ensure efficient efflux from the cell.

In some embodiments, a non-cyclical cultivation strategy is used to achieve anaerobic, micro-aerobic, or aerobic cultivation conditions.

In some embodiments, a cyclical cultivation strategy is used to alternate between anaerobic and aerobic cultivation conditions.

In some embodiments, the cultivation strategy includes limiting nutrients, such as limiting nitrogen, phosphate or oxygen.

In some embodiments, one or more C6 building blocks are produced by a single type of microorganism, e.g., a recombinant host containing one or more exogenous nucleic acids, using a non-cyclical or cyclical fermentation strategy.

In some embodiments, one or more C6 building blocks are produced by co-culturing more than one type of microorganism, e.g., two or more different recombinant hosts, with each host containing a particular set of exogenous nucleic acids, using a non-cyclical or cyclical fermentation strategy.

In some embodiments, one or more C6 building blocks are produced by successive fermentations, where the broth or centrate from the preceding fermentation is fed to a succession of fermentations as a source of feedstock, central metabolite or central precursor; finally producing the C6 building block.

This document also features a recombinant host comprising at least one exogenous nucleic acid encoding, for example, one or more of a formate dehydrogenase, enoyl-CoA reductase, trans-2-enoyl-CoA hydratase, 3-hydroxybutyryl-CoA dehydrogenase, acetyl-CoA C-acyltransferase, acetoacyl-CoA reductase, acetyl-CoA synthetase, acetyl-CoA carboxylase, a malic enzyme, puridine nucleotide transhydrogenase, glyceraldehyde-3P-dehydrogenase, acyl-CoA hydrolase, aldehyde dehydrogenase, thioesterase, cytochrome P450/ω-hydroxylase, alcohol dehydrogenase, 6-hydroxyhexanoate dehydrogenase, 6-oxohexanoate dehydrogenase, diamine transaminase, propionyl-CoA synthetase, and a carboxylate reductase, wherein said host comprises one or more deficiencies, for example, in glucose-6-phosphate isomerase, acetate kinase, an enzyme degrading pyruvate to lactate, enzymes mediating the degradation of phophoenolpyruvate to succinate, alcohol dehydrogenase, pyruvate decarboxylase, 2-oxoacid decarboxylase, triose phosphate isomerase, a glutamate dehydrogenase.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DETAILED DESCRIPTION

Figure 1:
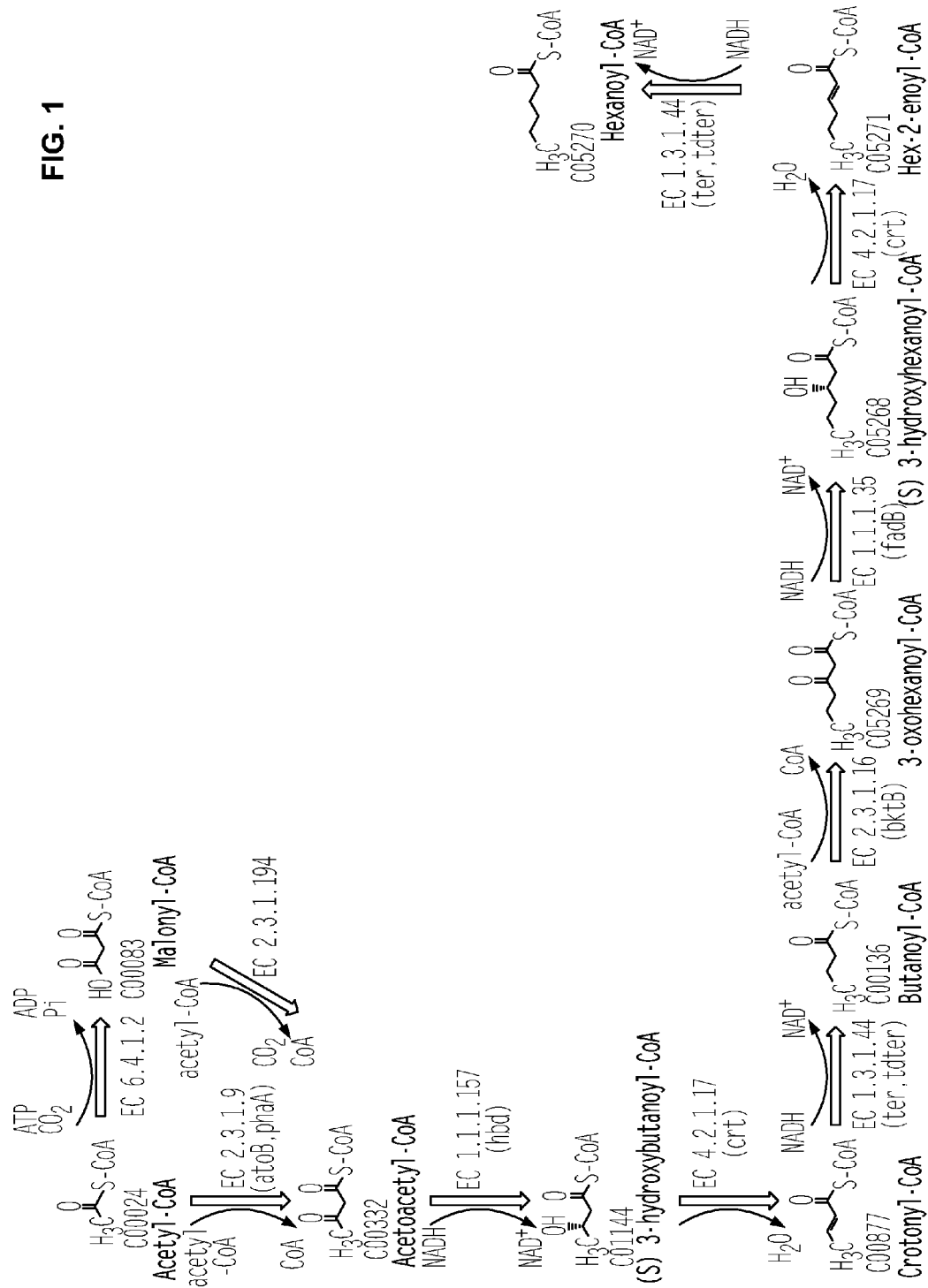
FIG. 1 is a schematic of an exemplary biochemical pathway leading to hexanoyl-CoA using NADH-dependent enzymes and with acetyl-CoA as a central metabolite.

In general, this document provides enzymes, non-natural pathways, cultivation strategies, feedstocks, host microorganisms and attenuations to the host's biochemical network, which generates a six carbon chain aliphatic backbone from central metabolites into which two terminal functional groups may be formed leading to the synthesis of adipic acid, caprolactam, 6-aminohexanoic acid, hexamethylenediamine or 1,6-hexanediol (referred to as "C6 building blocks" herein). As used herein, the term "central precursor" is used to denote a key metabolite in a pathway leading to the synthesis of C6 building blocks. The term "central metabolite" is used herein to denote a metabolite that is produced in all microorganisms to support growth.

As such, host microorganisms described herein can include endogenous pathways that can be manipulated such that one or more C6 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL. Engineered hosts can naturally express none or some (e.g., one or more, two or more, three or more, four or more, five or more, or six or more) of the enzymes of the pathways described herein. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. Thus, as described herein recombinant hosts can include nucleic acids encoding one or more of a β-ketothiolases, dehydrogenases, reductases, hydratases, monooxygenases, ω-hydroxylase or transaminases as described in more detail below.

In addition, the production of C6 building blocks can be performed in vitro using the isolated enzymes described herein, using a lysate (e.g., a cell lysate) from a host microorganism as a source of the enzymes, or using a plurality of lysates from different host microorganisms as the source of the enzymes.

The reactions of the pathways described herein can be performed in one or more host strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Moreover, such extracts include lysates (e.g. cell lysates) that can be used as sources of relevant enzymes. In the methods provided by the document, all the steps can be performed in host cells, all the steps can be performed using extracted enzymes, or some of the steps can be performed in cells and others can be performed using extracted enzymes.

Figure 2:
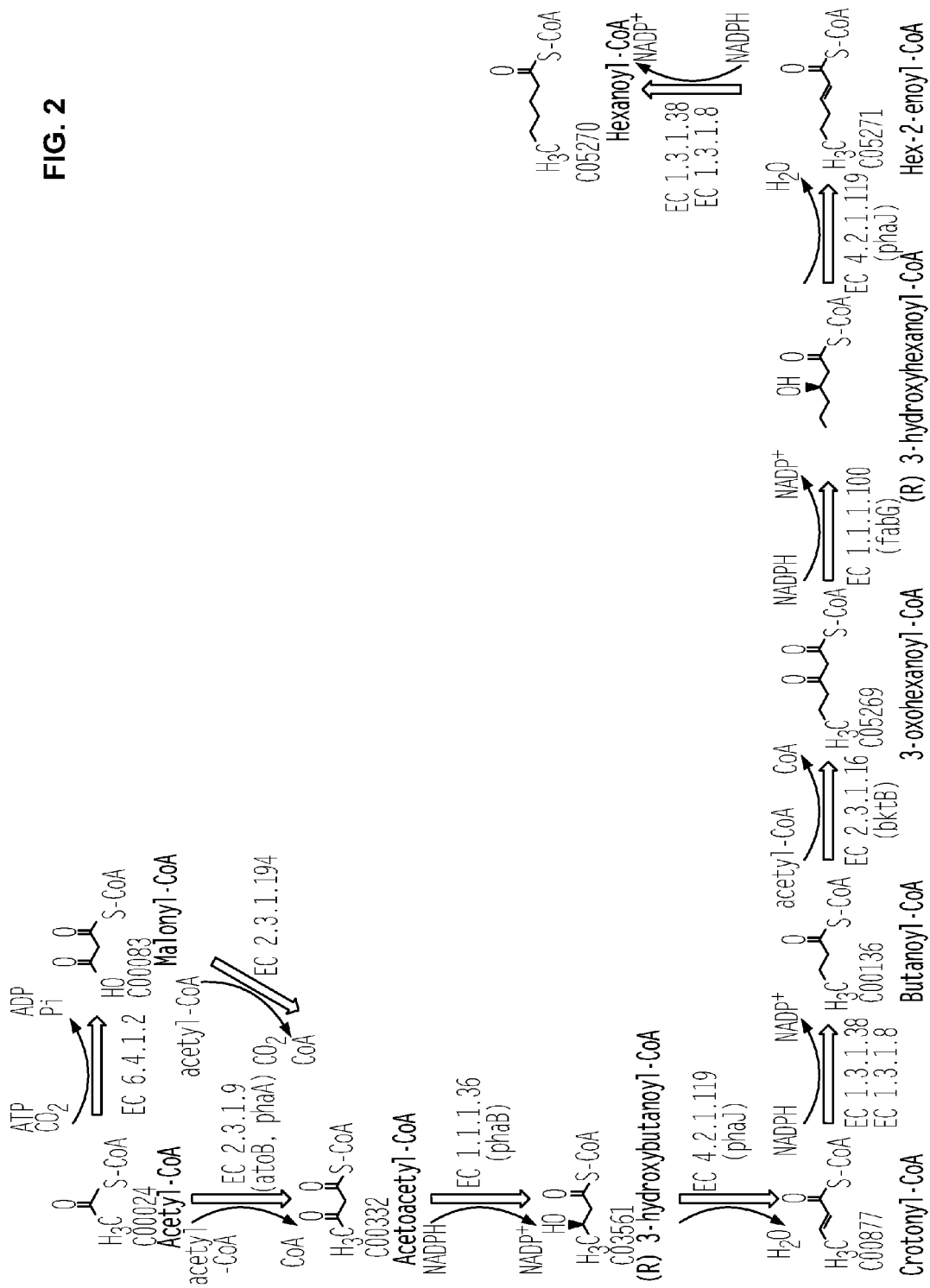
FIG. 2 is a schematic of an exemplary biochemical pathway leading to hexanoyl-CoA using NADPH-dependent enzymes and with acetyl-CoA as a central metabolite.

4.1 Enzymes Generating the C6 Aliphatic Backbone for Conversion to C6 Building Blocks As depicted in FIG. 1 and FIG. 2, the C6 aliphatic backbone for conversion to C6 building blocks can be formed from acetyl-CoA via two cycles of CoA-dependent carbon chain elongation using either NADH or NADPH dependent enzymes. In some embodiments, a CoA-dependent carbon chain elongation cycle comprises an acetyl-CoA C-acyltransferase, which converts acetyl-CoA to acetoacetyl-CoA and converts butanoyl-CoA to 3-oxohexanoyl-CoA, or an acetyl-CoA carboxylase, which converts acetyl-CoA to malonyl-CoA & an acetoacetyl-CoA synthase, which converts malonyl-CoA to acetoacetyl-CoA, a 3-hydroxybutyrl-CoA dehydrogenase, which converts acetoacetyl-CoA to 3-hydroxybutanoyl CoA or 3-oxoacyl-CoA reductase/3-hydroxyacyl-CoA dehydrogenase, which converts 3-oxohexanoyl-CoA to 3-hydroxyhexanoyl-CoA, an enoyl-CoA hydratase, which converts 3-hydroxybutanoyl-CoA to crotonyl-CoA and converts 3-hydroxyhexanoyl-CoA to hex-2-enoyl-CoA, and a trans-2-enoyl-CoA reductase, which converts crotonyl-CoA to butanoyl-CoA and converts hex-2-enoyl-CoA to hexanoyl-CoA.

In some embodiments, an acetyl-CoA C-acyltransferase may be classified under EC 2.3.1.9, such as the gene product of atoB or phaA, or classified under EC 2.3.1.16, such as the gene product of bktB.

The β-ketothiolase encoded by atoB or phaA accepts acetyl-CoA as substrates, forming butanoyl-CoA (Haywood et al., FEMS Microbiology Letters, 1988, 52, 91-96; Slater et al., Journal of Bacteriology, 1998, 180(8), 1979-1987).

The β-ketothiolase encoded by bktB from *Cupriavidus necator* accepts acetyl-CoA and butanoyl-CoA as substrates, forming the CoA-activated C6 aliphatic backbone (Haywood et al., FEMS Microbiology Letters, 1988, 52, 91-96; Slater et al., Journal of Bacteriology, 1998, 180(8), 1979-1987).

In some embodiments, an acetyl-CoA carboxylase may be classified under EC 6.4.1.2.

Conversion of acetyl-CoA to malonyl-CoA by acetyl-CoA carboxylase has been shown to increase the rate of fatty acid synthesis (Davis et al., The Journal of Biological Chemistry, 2000, 275(37), 28593-28598).

In some embodiments, an acetoacetyl-CoA synthase may be classified under EC 2.3.1.194.

It has been demonstrated that acetoacetyl-CoA synthase may be used as an irreversible substitute for the gene product of phaA in the carbon chain elongation associated with polyhydroxybutyrate synthesis (Matsumoto et al., Biosci. Biotechnol. Biochem., 2011, 75(2), 364-366).

In some embodiments, a 3-hydroxyacyl-CoA dehydrogenase may be classified under EC 1.1.1.35, such as the gene product of fadB, or a 3-hydroxybutyryl-CoA dehydrogenase may be classified under EC 1.1.1.157, such as the gene product of hbd, or an acetoacetyl-CoA reductase may be classified under EC 1.1.1.36, such as the gene product of phaB (Liu & Chen, Appl. Microbiol. Biotechnol., 2007, 76(5), 1153-1159; Shen et al., *Appl. Environ. Microbiol.*, 2011, 77(9), 2905-2915; Budde et al., Journal of Bacteriology, 2010, 192(20), 5319-5328).

In some embodiments, a 3-oxoacyl-CoA reductase may be classified under EC 1.1.1.100, such as the gene product of fabG (Budde et al., Journal of Bacteriology, 2010, 192(20), 5319-5328; Nomura et al., Appl. Environ. Microbiol., 2005, 71(8), 4297-4306).

In some embodiments, an enoyl-CoA hydratase may be classified under EC 4.2.1.17, such as the gene product of crt, or classed under EC 4.2.1.119, such as the gene product ofphaJ (Shen et al., *Appl. Environ. Microbiol.*, 2011, 77(9), 2905-2915; Fukui et al., Journal of Bacteriology, 1998, 180 (3), 667-673).

In some embodiments, a trans-2-enoyl-CoA reductase may be classified under EC 1.3.1.38, EC 1.3.1.8 or EC 1.3.1.44, such as the gene product of ter or tdter (Nishimaki et al., J. Biochem., 1984, 95, 1315-1321; Shen et al., *Appl. Environ. Microbiol.*, 2011, 77(9), 2905-2915; Bond-Watts et al., *Biochemistry*, 2012, 51, 6827-6837).

Figure 3:
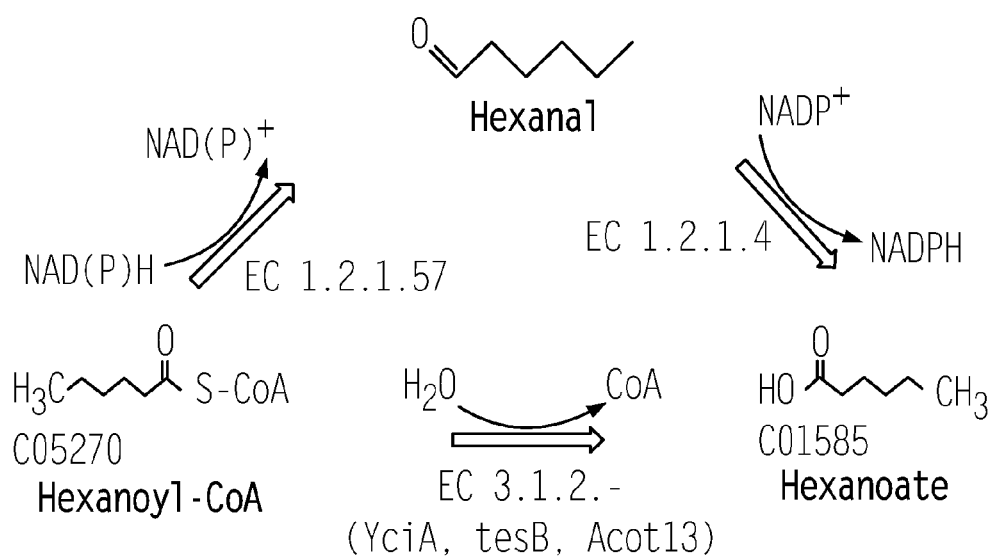
FIG. 3 is a schematic of exemplary biochemical pathways leading to hexanoate using hexanoyl-CoA as a central metabolite.
Figure 4:
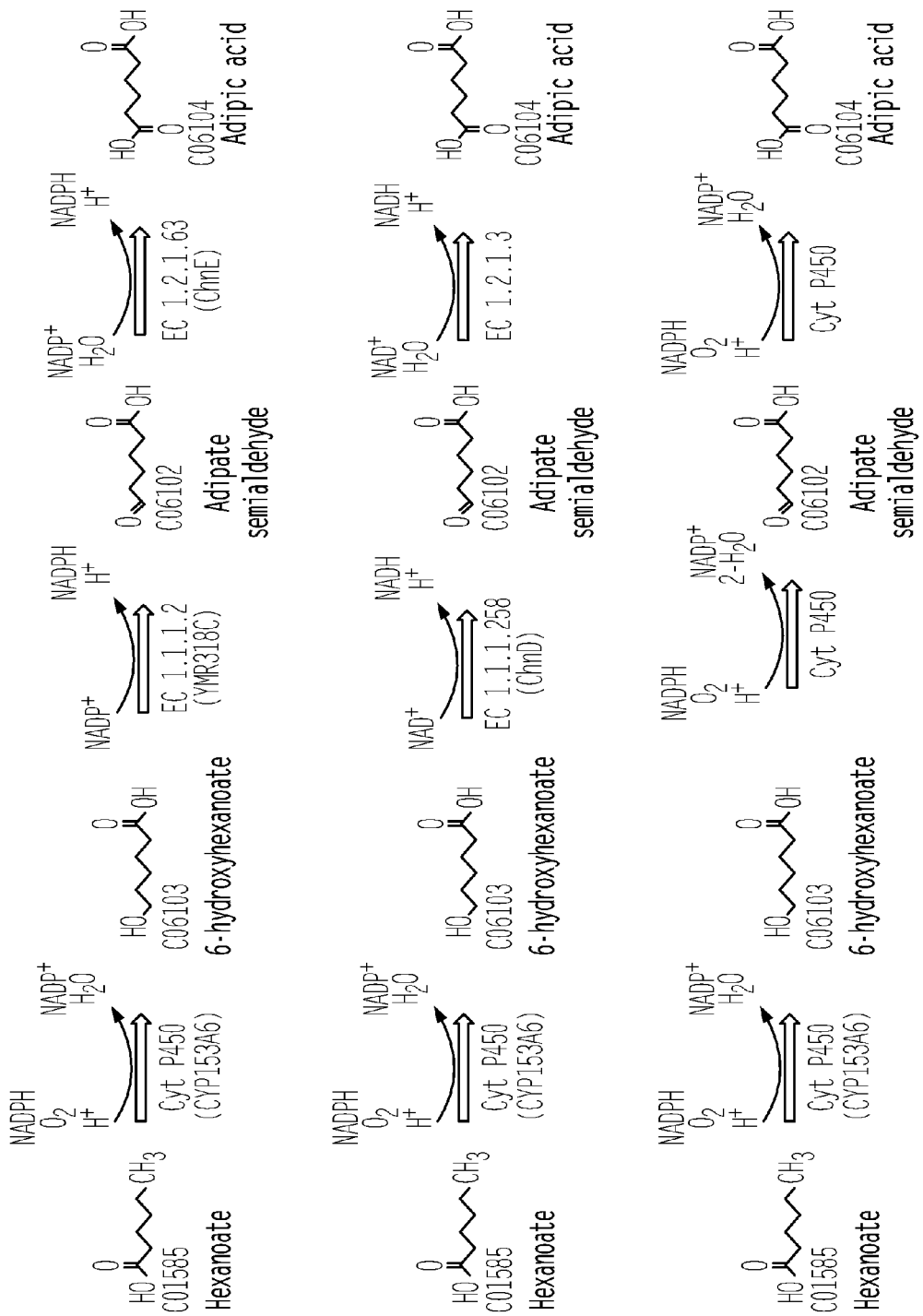
FIG. 4 is a schematic of exemplary biochemical pathways leading to adipic acid using hexanoate as a central precursor.

4.2 Enzymes Generating the Terminal Carboxyl Groups in the Biosynthesis of C6 Building Blocks As depicted in FIG. 3 and FIG. 4, the terminal carboxyl groups can be enzymatically formed using an acyl-CoA hydrolase, an aldehyde dehydrogenase, a 6-oxohexanoate dehydrogenase or a cytochrome P450/ω-hydroxylase.

In some embodiments, the first terminal carboxyl group leading to the synthesis of a C6 building block is enzymatically formed in hexanoyl-CoA by an acyl-CoA hydrolase or thioesterase classified under EC 3.1.2.-, resulting in the production of hexanoate. The acyl-CoA hydrolase or thioesterase can be the gene product of YciA, tesB or Acot13 (Cantu et al., Protein Science, 2010, 19, 1281-1295; Zhuang et al., Biochemistry, 2008, 47(9), 2789-2796; Naggert et al., Journal of Biological Chemistry, 1991, 266(17), 11044-11050).

In some embodiments, the first terminal carboxyl group leading to the synthesis of a C6 building block is enzymatically formed in hexanal by an aldehyde dehydrogenase classified under EC 1.2.1.4 (Ho & Weiner, Journal of Bacteriology, 2005, 187(3), 1067-1073), resulting in the production of hexanoate.

In some embodiments, the second terminal carboxyl group leading to the synthesis of adipic acid is enzymatically formed in adipate semialdehyde by an aldehyde dehydrogenase classified under EC 1.2.1.3 (Guerrillot & Vandecasteele, Eur. J. Biochem., 1977, 81, 185-192).

In some embodiments, the second terminal carboxyl group leading to the synthesis of adipic acid is enzymatically formed in adipate semialdehyde by a 6-oxohexanoate dehydrogenase classified under EC 1.2.1.63, such as the gene product of ChnE (Iwaki et al., Appl. Environ. Microbiol., 1999, 65(11), 5158-5162).

In some embodiments, the second terminal carboxyl group leading to the synthesis of adipic acid is enzymatically formed in adipate semialdehyde by a cytochrome P450 (Sanders et al., Journal of Lipid Research, 2005, 46(5), 1001-1008; Sanders et al., The FASEB Journal, 2008, 22(6), 2064-2071).

The utility of ω-oxidation in introducing carboxyl groups into alkanes has been demonstrated in the yeast *Candida tropicalis*, leading to the synthesis of adipic acid (Okuhara et al., Agr. Boil. Chem., 1971, 35(9), 1376-1380).

Figure 5:
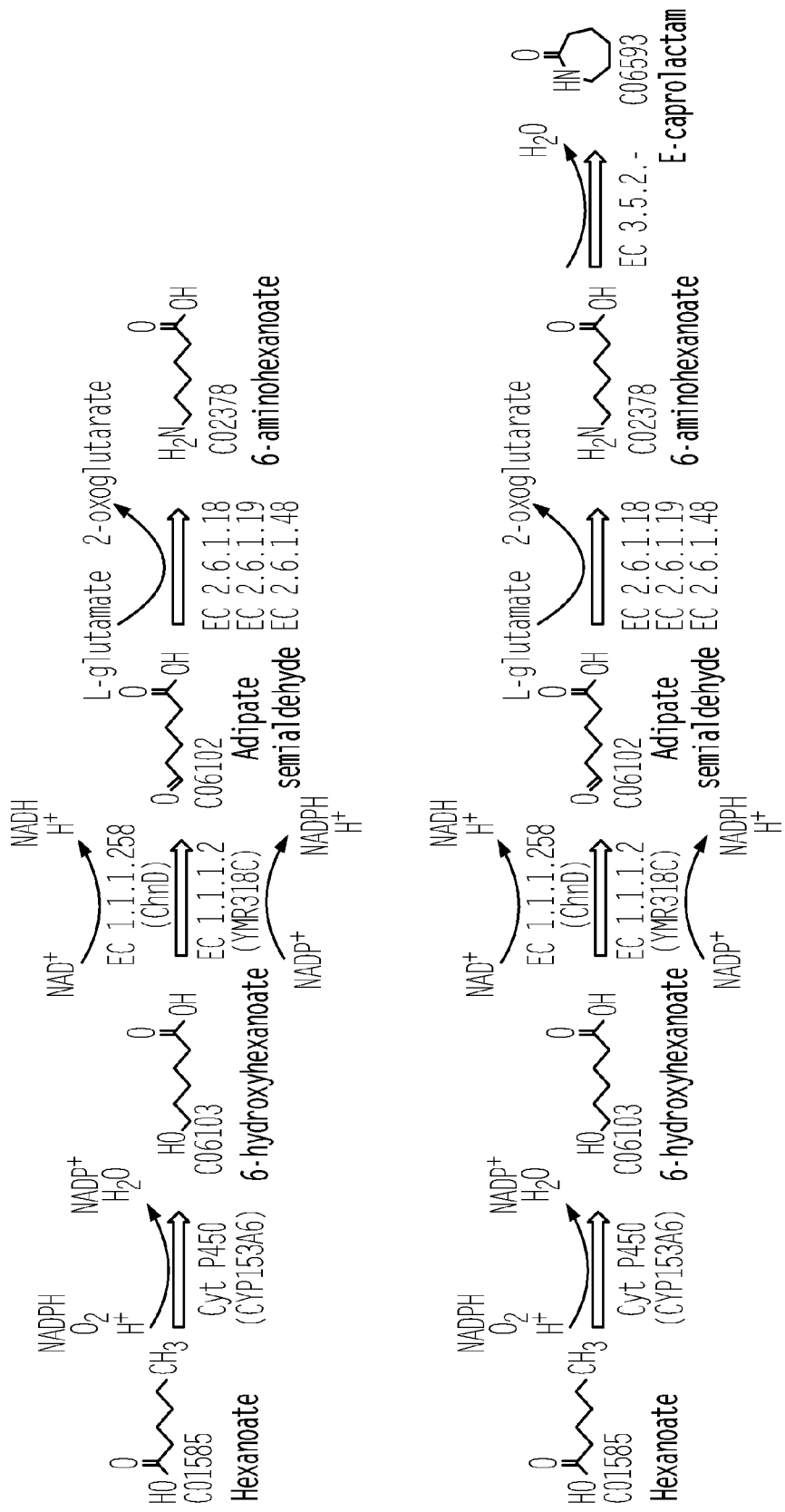
FIG. 5 is a schematic of exemplary biochemical pathways leading to 6-aminhexanoate using hexanoate as a central precursor.
Figure 6:
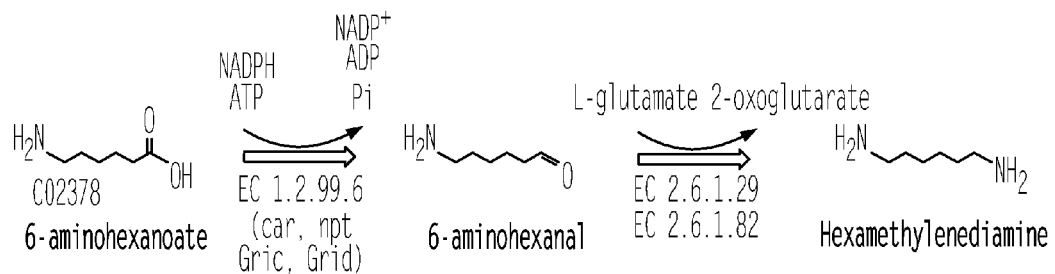
FIG. 6 is a schematic of an exemplary biochemical pathway leading to hexamethylenediamine using 6-aminhexanoate as a central precursor.

4.3 Enzymes Generating the Terminal Amine Groups in the Biosynthesis of C6 Building Blocks As depicted in FIG. 5 and FIG. 6, terminal amine groups can be enzymatically formed using a ω-transaminase or a diamine transaminase.

In some embodiments, the first terminal amine group leading to the synthesis of 6-aminohexanoic acid is enzymatically formed in adipate semialdehyde by a ω-transaminase classified under EC 2.6.1.18, such as obtained from *Vibrio fluvialis* or *Chromobacterium violaceum*, or classified under EC 2.6.1.19, such as obtained from *Streptomyces griseus*, or classified under 2.6.1.48, such as obtained from *Clostridium viride*.

The reversible ω-transaminase from *Chromobacterium violaceum* has demonstrated activity accepting 6-aminohexanoic acid as amino donor, thus forming the first terminal amine group in adipate seminaldehyde (Kaulmann et al., Enzyme and Microbial Technology, 2007, 41, 628-637).

The reversible 4-aminobubyrate:2-oxoglutarate transaminase from *Streptomyces griseus* has demonstrated activity for the conversion of 6-aminohexanoate to adipate semialdehyde (Yonaha et al., Eur. J. Biochem., 1985, 146, 101-106).

The reversible 5-aminovalerate transaminase from *Clostridium viride* has demonstrated activity for the conversion of 6-aminohexanoate to adipate semialdehyde (Barker et al., The Journal of Biological Chemistry, 1987, 262(19), 8994-9003).

In some embodiments, the second terminal amine group leading to the synthesis of hexamethylenediamine is enzymatically formed in 6-aminohexanal by a diamine transaminase classified under EC 2.6.1.29 or classified under EC 2.6.1.82, such as the gene product of YgjG.

The gene product of ygjG accepts a broad range of diamine carbon chain length substrates, such as putrescine, cadaverine and spermidine (Samsonova et al., BMC Microbiology, 2003, 3:2)

The diamine transaminase from *E. coli* strain B has demonstrated activity for 1,5 diaminopentane and 1,7 diaminoheptane, with 1,6 diaminohexane (HMD) expected to be active (Kim, The Journal of Chemistry, 1963, 239(3), 783-786).

Figure 7:
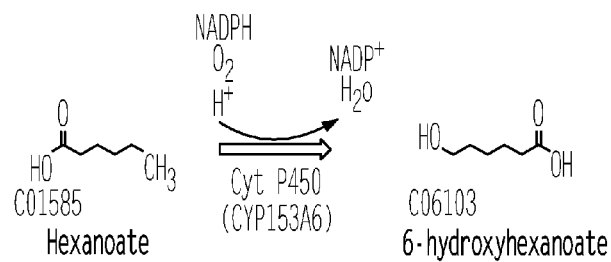
FIG. 7 is a schematic of an exemplary biochemical pathway leading to 6-hydroxyhexanoate using hexanoate as a central precursor.
Figure 8:
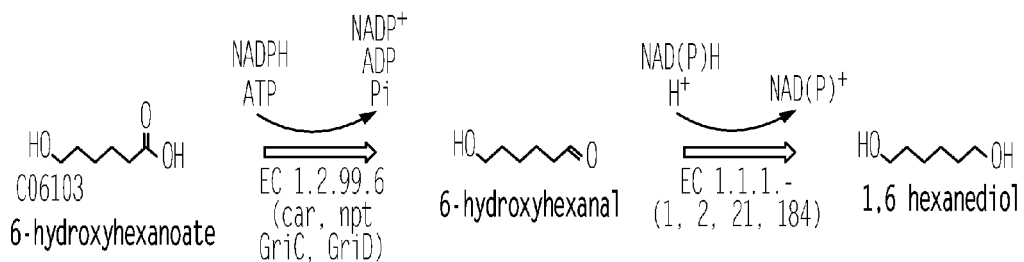
FIG. 8 is a schematic of an exemplary biochemical pathway leading to 1,6-hexanediol using 6-hydroxyhexanoate as a central precursor.

4.4 Enzymes Generating the Terminal Hydroxyl Groups in the Biosynthesis of C6 Building Blocks As depicted in FIG. 7 and FIG. 8, the terminal hydroxyl group can be enzymatically forming using a cytochrome P450, a monooxygenase or an alcohol dehydrogenase.

In some embodiments, the first terminal hydroxyl group leading to the synthesis of C6 building blocks is enzymatically formed in hexanoate by a monooxygenase, a cytochrome P450 or a ω-hydroxylase such as from the CYP153 family such as CYP153A6 (Van Beilen & Funhoff, Current Opinion in Biotechnology, 2005, 16, 308-314; Koch et al., Appl. Environ. Microbiol., 2009, 75(2), 337-344; Nieder and Shapiro, Journal of Bacteriology, 1975, 122(1), 93-98).

The substrate specificity of terminal ω-hydroxylase has been broadened successfully (Koch et al., Appl. Environ. Microbiol., 2009, 75(2), 337-344). Although, In some embodiments, the second terminal hydroxyl group leading to the synthesis of 1,6 hexanediol is enzymatically formed in 6-hydroxyhexanal by an alcohol dehydrogenase classified under EC 1.1.1.- (e.g., 1, 2, 21, or 184). Although non-terminal hydroxylation is observed in vitro for CYP153A6, in vivo only 1-hydroxylation occurs (Funhoff et al., Journal of Bacteriology, 2006, 188(14), 5220-5227).

4.5 Biochemical Pathways

4.5.1 Pathways to Hexanoyl-CoA as Precursor Leading to Central Precursors to C6 Building Blocks In some embodiments, hexanoyl-CoA is synthesized from the central metabolite, acetyl-CoA, by conversion of acetyl-CoA to acetoacetyl-CoA by acetoacetyl-CoA thiolase (EC 2.3.1.9), such as the gene product of atoB or phaA, or by acetyl-CoA carboxylase (EC 6.4.1.2) & acetoacetyl-CoA synthase (EC 2.3.1.194) via malonyl-CoA; followed by conversion of acetoacetyl-CoA to (S) 3-hydroxybutanoyl-CoA by a 3-hydroxybutyryl-CoA dehydrogenase (EC 1.1.1.157) such as the gene product of hbd; followed by conversion of (S) 3-hydroxybutanoyl-CoA to crotonyl-CoA by enoyl-CoA hydratase (EC 4.2.1.17) such as the gene product of crt; followed by conversion of crotonyl-CoA to butanoyl-CoA by trans-2-enoyl-CoA reductase (EC 1.3.1.44) such as the gene product of ter; followed by conversion of butanoyl-CoA to 3-oxo-hexanoyl-CoA by acetyl-CoA C-acyltransferase (EC 2.3.1.16) such as the gene product of bktB; followed by conversion of 3-oxo-hexanoyl-CoA to (S) 3-hydroxyhexanoyl-CoA by 3-hydroxyacyl-CoA dehydrogenase (EC 1.1.1.35) such as the gene product of fabB; followed by conversion of (S) 3-hydroxyhexanoyl-CoA to hex-2-enoyl-CoA by enoyl-CoA hydratase (EC 4.2.1.17) such as the gene product of crt; followed by conversion of hex-2-enoyl-CoA to hexanoyl-CoA by trans-2-enoyl-CoA reductase (EC 1.3.1.44) such as the gene product of ter or tdter. See FIG. 1.

In some embodiments, hexanoyl-CoA is synthesized from the central metabolite, acetyl-CoA, by conversion of acetyl-CoA to acetoacetyl-CoA by acetoacetyl-CoA thiolase (EC 2.3.1.9), such as the gene product of atoB or phaA, or by acetyl-CoA carboxylase (EC 6.4.1.2) & acetoacetyl-CoA synthase (EC 2.3.1.194) via malonyl-CoA; followed by conversion of acetoacetyl-CoA to (R) 3-hydroxybutanoyl-CoA by a 3-acetoacetyl-CoA reductase (EC 1.1.1.36) such as the gene product of phaB; followed by conversion of (R) 3-hydroxybutanoyl-CoA to crotonyl-CoA by enoyl-CoA hydratase (EC 4.2.1.119) such as the gene product of phaJ; followed by conversion of crotonyl-CoA to butanoyl-CoA by trans-2-enoyl-CoA reductase (EC 1.3.1.38); followed by conversion of butanoyl-CoA to 3-oxo-hexanoyl-CoA by acetyl-CoA C-acyltransferase (EC 2.3.1.16) such as the gene product of bktB; followed by conversion of 3-oxo-hexanoyl-CoA to (R) 3-hydroxyhexanoyl-CoA by 3-oxoacyl-CoA reductase (EC 1.1.1.100) such as the gene product offabG; followed by conversion of (R) 3-hydroxyhexanoyl-CoA to hex-2-enoyl-CoA by enoyl-CoA hydratase (EC 4.2.1.119) such as the gene product of phaJ; followed by conversion of hex-2-enoyl-CoA to hexanoyl-CoA by trans-2-enoyl-CoA reductase (EC 1.3.1.38). See FIG. 2.

4.5.2 Pathways Using Hexanoyl-CoA as Precursor Leading to the Central Precursor Hexanoate In some embodiments, hexanoate is synthesized from the central metabolite, hexanoyl-CoA, by conversion of hexanoyl-CoA to hexanoate by acyl-CoA hydrolase or thioesterase (EC 3.1.2.-) such as the gene product of YciA, tesB or Acot13.

In some embodiments, hexanoate is synthesized from the central metabolite, hexanoyl-CoA, by conversion of hexanoyl-CoA to hexanal by butanal dehydrogenase (EC 1.2.1.57); followed by conversion of hexanal to hexanoate by aldehyde dehydrogenase (EC 1.2.1.4). See FIG. 3.

The conversion of hexanoyl-CoA to hexanal has been demonstrated for both NADH and NADPH as co-factors (Palosaari and Rogers, Journal of Bacteriology, 1988, 170(7), 2971-2976).

4.5.3. Pathways Using Hexanoate as Central Precursor to Adipic Acid

In some embodiments, adipic acid is synthesized from the central precursor, hexanoate, by conversion of hexanoate to 6-hydroxyhexanoate by monooxygenase or cytochrome P450 such as from the CYP153 family such as CYP153A6; followed by conversion of 6-hydroxyhexanoate to adipate semialdehyde by alcohol dehydrogenase (EC 1.1.1.2) such as the gene product of YMR318C; followed by conversion of adipate semialdehyde to adipic acid by 6-oxohexanoate dehydrogenase (EC 1.2.1.63). See FIG. 4.

The alcohol dehydrogenase encoded by YMR318C has broad substrate specificity, including the oxidation of C6 alcohols.

In some embodiments, adipic acid is synthesized from the central precursor, hexanoate, by conversion of hexanoate to 6-hydroxyhexanoate by monooxygenase or cytochrome P450 such as from the CYP153 family such as CYP153A6; followed by conversion of 6-hydroxyhexanoate to adipate semialdehyde by 6-hydroxyhexanoate dehydrogenase (EC 1.1.1.258) such as the gene product of ChnD (Iwaki et al., Appl. Environ. Microbiol., 1999, 65(11), 5158-5162); followed by conversion of adipate semialdehyde to adipic acid by aldehyde dehydrogenase (EC 1.2.1.3). See FIG. 4.

In some embodiments, adipic acid is synthesized from the central precursor, hexanoate, by conversion of hexanoate to 6-hydroxyhexanoate by monooxygenase or cytochrome P450 such as from the CYP153 family such as CYP153A6; followed by conversion of 6-hydroxyhexanoate to adipate semialdehyde by cytochrome P450 (Sanders et al., Journal of Lipid Research, 2005, 46(5), 1001-1008; Sanders et al., The FASEB Journal, 2008, 22(6), 2064-2071); followed by conversion of adipate semialdehyde to adipic acid by cytochrome P450. See FIG. 4.

4.5.4 Pathway Using Hexanoate as Central Precursor to 6-aminohexanoate and ε-caprolactam In some embodiments, 6-aminohexanoate is synthesized from the central precursor, hexanoate, by conversion of hexanoate to 6-hydroxyhexanoate by monooxygenase or cytochrome P450 such as from the CYP153 family such as CYP153A6; followed by conversion of 6-hydroxyhexanoate to adipate semialdehyde by alcohol dehydrogenase (EC 1.1.1.2) or 6-hydroxyhexanoate dehydrogenase (EC 1.1.1.258); followed by conversion of adipate semialdehyde to 6-aminohexanoate by ω-transaminase (EC 2.6.1.18, EC 2.6.1.19, EC 2.6.1.48). See FIG. 5.

In some embodiments, ε-caprolactam is synthesized from the central precursor, hexanoate, by conversion of hexanoate to 6-hydroxyhexanoate by monooxygenase or cytochrome P450 such as from the CYP153 family such as CYP153A6; followed by conversion of 6-hydroxyhexanoate to adipate semialdehyde by alcohol dehydrogenase (EC 1.1.1.2) or 6-hydroxyhexanoate dehydrogenase (EC 1.1.1.258); followed by conversion of adipate semialdehyde to 6-aminohexanoate by ω-transaminase (EC 2.6.1.18, EC 2.6.1.19, EC 2.6.1.48); followed by conversion of 6-aminohexanoate to ε-caprolactam by hydrolase (EC 3.5.2.-). See FIG. 5.

4.5.5 Pathway Using 6-aminohexanoate as Central Precursor to Hexamethylenediamine In some embodiments, hexamethylenediamine is synthesized from the central precursor, 6-aminohexanoate, by conversion of 6-aminohexanoate to 6-aminohexanal by carboxylate reductase (EC 1.2.99.6) such as the gene product of car alongside the gene product of npt or the gene product of GriC & GriD (Suzuki et al., J. Antibiot., 2007, 60(6), 380-387); followed by conversion of 6-aminohexanal to hexamethylenediamine by diamine transaminase (EC 2.6.1.29, EC 2.6.1.82). See FIG. 6.

The carboxylate reductase encoded by the gene product of car and enhancer npt has broad substrate specificity, including terminal difunctional C4 and C5 carboxylic acids (Venkitasubramanian et al., Enzyme and Microbial Technology, 2008, 42, 130-137).

4.5.6 Pathways Using Hexanoate as Central Precursor to 1,6-hexanediol

In some embodiments, 6-hydroxyhexanoate is synthesized from the central precursor, hexanoate, by conversion of hexanoate to 6-hydroxyhexanoate by by monooxygenase or cytochrome P450 such as from the CYP153 family such as CYP153A6. See FIG. 7.

In some embodiments, 1,6 hexanediol is synthesized from the central precursor, 6-hydroxyhexanoate, by conversion of 6-hydroxyhexanoate to 6-hydroxyhexanal by carboxylate reductase (EC 1.2.99.6) such as the gene product of car alongside the gene product of npt; followed by conversion of 6-hydroxyhexanal to 1,6 hexanediol by an alcohol dehydrogenase (e.g., EC 1.1.1.1, EC 1.1.1.2, EC 1.1.1.21, or EC 1.1.1.184) (Liu et al., Microbiology, 2009, 155, 2078-2085).

4.6 Cultivation Strategy

In some embodiments, one or more C6 building blocks are biosynthesized in a recombinant host using anaerobic, aerobic or micro-aerobic cultivation conditions. A non-cyclical or a cyclical cultivation strategy can be used to achieve the desired cultivation conditions. For example, a non-cyclical strategy can be used to achieve anaerobic, aerobic or microaerobic cultivation conditions.

In some embodiments, a cyclical cultivation strategy can be used to alternate between anaerobic cultivation conditions and aerobic cultivation conditions.

In some embodiments, the cultivation strategy entails nutrient limitation either via nitrogen, phosphate or oxygen limitation.

In some embodiments, one or more C6 building blocks are produced by a single microorganism via a non-cyclical or cyclical fermentation strategy.

In some embodiments, one or more C6 building blocks are produced by co-culturing more than one microorganism via a non-cyclical or cyclical fermentation strategy.

In some embodiments, one or more C6 building blocks are produced by successive fermentations, where the broth or centrate from the preceding fermentation is fed to a succession of fermentations as feedstock; finally producing the C6 building block.

In some embodiments, a cell retention strategy using, for example, ceramic hollow fiber membranes is employed to achieve and maintain a high cell density during either fed-batch or continuous fermentation.

In some embodiments, the principal carbon source fed to the fermentation in the synthesis of C6 building block derives from biological or non-biological feedstocks.

In some embodiments, the biological feedstock is, includes, or derives from, monosaccharides, disaccharides, lignocellulose, hemicellulose, cellulose, lignin such as levulinic acid and furfural, lignin, triglycerides such as glycerol and fatty acids, agricultural waste or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., *Appl. Biochem. Biotechnol.*, 2012, 166, 1801-1813; Yang et al., Biotechnology for Biofuels, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such benzoate analogues has been demonstrated in several microorganisms such as *Pseudomonas putida, Cupriavidus necator* (Bugg et al., Current Opinion in Biotechnology, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassaya, corn and other argricultural sources has been demonstrated for several microorganism such as *Escherichia coli, Corynebacterium glutamicum* and *Lactobacillus delbrueckii* and *Lactococcus lactis* (see, e.g., Hermann et al, *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock is or derives from natural gas, syngas, $CO_2/H_2$, methanol, ethanol, non-volatile residue (NVR) or a caustic wash waste stream from cyclohexane oxidation processes.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1), 152-156).

In some embodiments, the host is a prokaryote. For example, the prokaryote can be from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing C6 building blocks.

In some embodiments, the host is a eukaryote. For example, the eukaryote can be from the genus *Aspergillus* such as *Aspergillus niger*; from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing C6 building blocks.

4.7 Metabolic Engineering

The present document provides methods involving less than all the steps described for all the above pathways. Such methods can involve, for example, one, two, three, four, five, six, seven, eight, nine, ten, or more of such steps. Where less than all the steps are included in such a method, the first step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, eleven, twelve or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined in section 4.5 are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined in section 4.5 are gene dosed, i.e., overexpressed, into the resulting genetically modified organism via episomal or chromosomal integration approaches.

In some embodiments, genome-scale system biology techniques such as Flux Balance Analysis are utilized to devise genome scale attenuation or knockout strategies for directing carbon flux to a C6 building block.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data are utilized to inform or support genome-scale system biology techniques, thereby devising genome scale attenuation or knockout strategies in directing carbon flux to a C6 building block.

In some embodiments, the host microorganism's tolerance to high concentrations of a C6 building block is improved through continuous cultivation in a selective environment.

In some embodiments, the host microorganism's biochemical network is attenuated or augmented to (1) ensure the intracellular availability of acetyl-CoA, (2) create an NADH or NADPH imbalance that may only be balanced via the formation of C6 building blocks, (3) prevent degradation of central metabolites, central precursors leading to and including C6 building blocks and (4) ensure efficient efflux from the cell.

In some embodiments requiring the intracellular availability of acetyl-CoA for C6 building block synthesis, a phosphotransacetylase generating acetate such as pta is attenuated (Shen et al., *Appl. Environ. Microbiol.*, 2011, 77(9), 2905-2915).

In some embodiments requiring the intracellular availability of acetyl-CoA for C6 building Block synthesis, a gene in an acetate synthesis pathway encoding an acetate kinase, such as ack, is attenuated.

In some embodiments requiring the intracellular availability of acetyl-CoA and NADH for C6 building block synthesis, a gene encoding the degradation of pyruvate to lactate such as ldhA is attenuated (Shen et al., *Appl. Environ. Microbiol.*, 2011, 77(9), 2905-2915).

In some embodiments requiring the intracellular availability of acetyl-CoA and NADH for C6 building block synthesis, genes encoding the degradation of phophoenolpyruvate to succinate such as frdBC are attenuated (see, e.g., Shen et al., 2011, supra).

In some embodiments requiring the intracellular availability of acetyl-CoA and NADH for C6 building block synthesis, a gene encoding the degradation of acetyl-CoA to ethanol such as the alcohol dehydrogenase encoded by adhE is attenuated (Shen et al., 2011, supra).

In some embodiments, a gene encoding the degradation of pyruvate to ethanol such as pyruvate decarboxylase is attenuated.

In some embodiments, a gene encoding the generation of isobutanol such as a 2-oxoacid decarboxylase is attenuated.

In some embodiments requiring the intracellular availability of acetyl-CoA for C6 building block synthesis, acetyl-CoA synthetase such as the gene product of acs is overexpressed in the microorganism (Satoh et al., *Journal of Bioscience and Bioengineering*, 2003, 95(4), 335-341).

In some embodiments, carbon flux is directed into the pentose phosphate cycle by attenuating glucose-6-phosphate isomerase (EC 5.3.1.9).

In some embodiments, where pathways require excess NADH co-factor for C6 building block synthesis, a formate dehydrogenase gene is overexpressed in the host organism (Shen et al., 2011, supra).

In some embodiments, where pathways require excess NADPH co-factor in the synthesis of C6 building block, a puridine nucleotide transhydrogenase gene such as UdhA is overexpressed in the host organisms (Brigham et al., *Advanced Biofuels and Bioproducts,* 2012, Chapter 39, 1065-1090).

In some embodiments, where pathways require excess NADPH co-factor in the synthesis of C6 building block, a glyceraldehyde-3P-dehydrogenase gene such as GapN is overexpressed in the host organisms (Brigham et al., 2012, supra).

In some embodiments, where pathways require excess NADPH co-factor in the synthesis of C6 building block, a malic enzyme gene such as maeA or maeB is overexpressed in the host organisms (Brigham et al., 2012, supra).

In some embodiments, where pathways require excess NADPH co-factor in the synthesis of C6 building block, a glucose-6-phosphate dehydrogenase gene such as zwf is overexpressed in the host organisms (Lim et al., *Journal of Bioscience and Bioengineering,* 2002, 93(6), 543-549).

In some embodiments, where pathways require excess NADPH co-factor in the synthesis of C6 building block, a fructose 1,6 diphosphatase gene such as fbp is overexpressed in the host organisms (Becker et al., *Journal of Biotechnology,* 2007, 132, 99-109).

In some embodiments, where pathways require excess NADPH co-factor in the synthesis of C6 building blocks, triose phosphate isomerase (EC 5.3.1.1) is attenuated.

In some embodiments, where pathways require excess NADPH co-factor in the synthesis of C6 building blocks, a glucose dehydrogenase such as the gene product of gdh is overexpressed in the host organism (Satoh et al., Journal of Bioscience and Bioengineering, 2003, 95(4), 335-341).

In some embodiments, enzymes facilitating the conversion of NADPH to NADH are attenuated, such as the NADH generation cycle that may be generated via inter-conversion of glutamate dehydrogenases in EC 1.4.1.2 (NADH-specific) and EC 1.4.1.4 (NADPH-specific).

In some embodiments, glutamate dehydrogenases (EC 1.4.1.3) that utilize both NADH and NADPH are co-factors are attenuated.

In some embodiments, membrane-bound cytochrome P450/ω-hydroxylases are solubilized via truncation of the N-terminal region that anchors the P450 to the endoplasmic reticulum (Scheller et al., The Journal of Biological Chemistry, 1994, 269(17), 12779 0 12783).

In some embodiments using hosts that naturally accumulate polyhydroxyalkanoates, the polymer synthase enzymes can be attenuated in the host strain.

In some embodiments requiring the intracellular availability of butanoyl-CoA for C6 building block synthesis, a propionyl-CoA synthetase such as the gene product of PrpE-RS is overexpressed in the microorganism (Rajashekhara & Watanabe, FEBS Letters, 2004, 556, 143-147).

In some embodiments, β-oxidation enzymes degrading central metabolites and central precursors leading to and including C6 building blocks are attenuated.

In some embodiments, enzymes activating C6 building blocks via Coenzyme A esterification such as CoA-ligases are attenuated.

In some embodiments, the efflux of a C6 building block across the cell membrane to the extracellular media is enhanced or amplified by genetically engineering structural modifications to the cell membrane or increasing any associated transporter activity for a C6 building block.

The invention will be further described in the following examples, which do not limit the scope of the invention described in the claims.

EXAMPLES

Example 1

Genome-scale Attenuation Strategy for Cyclical Synthesis of Adipic Acid from Glucose in *Saccharomyces cerevisiae*

Genome-scale Flux Balance Analysis was undertaken using the genome-scale model for *Saccharomyces cerevisiae* designated iMM904 (Mo et al., BMC Systems Biology, 2009, 3(37), 1-17).

The IMM904 model was extended by including ω-oxidation pathways as outlined in published work for eukaryotic organisms (Sanders et al., *Journal of Lipid Research*, 2005, 46(5), 1001-1008). Furthermore, the β-oxidation reactions in the peroxisome of the iMM904 model were extended and relevant membrane transport reactions were included. The inactivation of a fumarate reductase was required during validation of the extended model to align model fluxes with experimental flux data.

The NADH-specific enzymatic reactions outlined in FIG. 1 were incorporated into the model.

Allowance was made for the membrane transport of hexanoic acid and adipic acid to and from the extracellular media.

The stoichiometric balance of NADH in the production of 1-butanol in *E. coli* is far more efficient when overexpressing formate dehydrogenase (Shen et al., *Appl. Environ. Microbiol.*, 2011, 77(9), 2905-2915). The iMM904 model includes formate dehydrogenase, but lacked pyruvate formate lyase activity, which was included into the *Saccharomyces cerevisiae* model.

The co-factor specificity of NAD(H) or NADP(H) dependent enzymes was assessed and where published literature was not unequivocal in terms of specificity, a promiscuous enzyme was assumed.

The metabolic engineering workbench, Optflux, was used to search the solution space associated with the biochemical network for attenuation strategies that (1) produce hexanoate anaerobically from glucose, followed by (2) production of adipate aerobically from the extracellular hexanoate, whilst co-feeding glucose as carbon and energy source.

The optimization trials found four beneficial attenuations; viz. (1) attenuating glucose-6-phosphate isomerase, directing flux into the pentose phosphate cycle; (2) attenuating pyruvate decarboxylase or alcohol dehydrogenase, preventing ethanol production; (3) attenuating 2-oxoacid decarboxylase, preventing isobutanol production and (4) inactivating β-oxidation, preventing central precursor, central metabolite and adipic acid degradation.

The attenuations in this *S. cerevisiae* mutant using glucose as carbon and energy source, favored the balancing of NADH via the production of hexanoic acid as a means of maximizing biomass growth.

Overexpression of formate dehydrogenase in the *S. cerevisiae* mutant eliminated the by-product formation of formate and pyruvate, producing hexanoate with a molar yield of 0.62 [(mol hexanoate)/(mol glucose)].

Cycling from anaerobic to aerobic cultivation, while maintaining a glucose feed rate to match the growth rate under anaerobic conditions, resulted in an overall molar yield of 0.38 [(mol adipate)/(mol total glucose)].

In-silico attenuation of the biochemical network using a validated model determined that a cultivation strategy, cycling between anaerobic and aerobic conditions, produces predominantly adipic acid from the fed glucose.

Example 2

Genome-scale Attenuation Strategy for Micro-aerobic Synthesis from Glucose using NADH Imbalance to Direct Carbon Flux Towards Adipic Acid in *Saccharomyces Cerevisiae*

The iMM904 model outlined in Example 1 was utilized to assess the non-cyclical production of adipic acid using glucose as carbon and energy source under micro-aerobic, substrate oxidation and growth limiting cultivation conditions.

Using the extended iMM904 model and the metabolic engineering workbench, Optflux; optimization trials found an optimal attenuation strategy including: (1) attenuating hexanoate transport to the extracellular media; (2) attenuating ethanol excretion to the extracellular media; (3) attenuating 2-hydroxybutyrate oxidoreductase, preventing 2-hydroxybutyrate production; (4) attenuating DL glycerol-3-phosphatase, preventing glycerol production and (5) attenuating malate dehydrogenase, preventing inter-conversion of NADH to NADPH.

The resulting *S. cerevisiae* mutant produces adipate as the most advantageous means of balancing NADH to maximize biomass growth, producing adipate with a molar yield of 0.71 [(mol adipate)/(mol glucose)].

In-silico attenuation of the biochemical network using a validated model determined that a non-cyclical cultivation strategy under micro-aerobic conditions produces predominantly adipic acid from the fed glucose.

Example 3

Genome-scale Attenuation Strategy for Aerobic Synthesis from Glucose Using NADPH Imbalance to Direct Carbon Flux Towards Adipic Acid in *Saccharomyces Cerevisiae*

The iMM904 model outlined in Example 1 was utilized to assess the non-cyclical production of adipic acid using glucose as carbon and energy source under aerobic cultivation and growth limiting conditions.

The NADH-specific enzymatic reactions outlined in FIG. 1 were replaced by the equivalent NADPH-specific enzymatic reactions outlined in FIG. 2.

Using the extended iMM904 model and the metabolic engineering workbench, Optflux; optimization trials found an optimal attenuation strategy including; (1) attenuating triose phosphate isomerase/phosphoglucose isomerase, redirecting flux into the pentose phosphate cycle; (2) preventing the inter-conversion of NADPH to NADH, by attenuating the NADH-dependent glutamate dehydrogenase and proline oxidase.

The resulting *S. cerevisiae* mutant produces adipate as the most advantageous means of balancing NADPH to maximize biomass growth, producing adipate with a molar yield of 0.4 [(mol adipate)/(mol glucose)].

In-silico attenuation of the biochemical network using a validated model determined that a non-cyclical cultivation strategy under aerobic conditions produces predominantly adipic acid from the fed glucose.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method for biosynthesizing one or more products selected from the group consisting of adipic acid, 6-aminohexanoic acid, hexamethylenediamine, caprolactam, and 1,6-hexanediol, said method comprising enzymatically synthesizing hexanoyl-CoA and enzymatically forming, in one or more steps, two terminal functional groups selected from the group consisting of carboxyl, amine, and hydroxyl groups in hexanoyl-CoA to produce the one or more products.

2. The method of claim 1, wherein said two terminal functional groups are the same.

3. The method of claim 1, wherein said two terminal functional groups are different.

4. The method of claim 1, wherein hexanoyl-CoA is enzymatically synthesized from acetyl-CoA via two cycles of CoA-dependent carbon chain elongation using either NADH or NADPH dependent enzymes.

5. The method of claim 1, comprising forming a first terminal carboxyl group in hexanoyl CoA using a thioesterase to produce hexanoate.

6. The method of claim 5, wherein said thioesterase is encoded by YciA, tesB or Acot13.

7. The method of claim 1, comprising converting hexanoyl-CoA to hexanal by a butanal dehydrogenase classified under EC 1.2.1.57 before forming a first terminal carboxyl group in hexanal.

8. The method of claim 7, comprising producing hexanoate by forming a first terminal carboxyl group in hexanal by an aldehyde dehydrogenase classified under EC 1.2.1.4.

9. The method of claim 5, further comprising converting hexanoate to adipic acid, 6-aminohexanoic acid, hexamethylenediamine, ϵcaprolactam or 1,6 hexanediol with one or more enzymatic conversions, wherein one of said enzymatic conversions introduces the second terminal functional group.

10. The method of claim 9, comprising converting hexanoate to 6-hydroxyhexanoate using a cytochrome P450/ω-hydroxylase.

11. The method of claim 10, wherein said cytochrome P450/ω-hydroxylase is from the family CYP153 such as CYP153A6.

12. The method of claim 10, comprising converting 6-hydroxyhexanoate to adipate semialdehyde using (i) an alcohol dehydrogenase, (ii) a 6-hydroxyhexanoate dehydrogenase or (iii) a cytochrome P450/ω-hydroxylase.

13. The method of claim 12, wherein said alcohol dehydrogenase is encoded by YMR318C.

14. The method of claim 12, wherein said 6-hydroxyhexanoate dehydrogenase is encoded by ChnD.

15. The method of claim 12, comprising producing adipic acid by forming the second terminal functional group in adipate semialdehyde using (i) an aldehyde dehydrogenase classified under EC 1.2.1.3, (ii) a 6-oxohexanoate dehydrogenase classified under EC 1.2.1.63 or (iii) a cytochrome P450/ω-hydroxylase.

16. The method of claim 15, wherein said 6-oxohexanoate dehydrogenase is encoded by ChnE.

17. The method of claim 9, comprising producing 6-aminohexanoic acid by forming the second terminal functional group in adipate semialdehyde using an ω-transaminase classified under EC 2.61.18, EC 2.6.1.19 or EC 2.6.1.48.

18. The method of claim 1, comprising producing ϵ-caprolactam from 6-aminohexanoic acid using a lactamase classified under EC 3.5.2.

19. The method of claim 18, comprising converting 6-aminohexanoic acid to 6-aminohexanal using a carboxylate reductase classified under EC 1.2.99.6.

20. The method of claim 1, comprising producing hexamethylenediamine by forming a second terminal functional group in 6-aminohexanal using a diamine transaminase classified under EC 2.6.1.29 or EC 2.6.1.82.

21. The method of claim 19, wherein said carboxylate reductase is encoded by car alongside the gene product of npt.

22. The method of claim 19, wherein said carboxylate reductase is encoded by GriC & GriD.

23. The method of claim 1, comprising producing 1,6 hexanediol by forming the second terminal functional group in 6-hydroxyhexanal using an alcohol dehydrogenase classified under EC 1.1.1.-(1,2,21,184).

24. The method of claim 1, wherein said method is performed in a recombinant host.

25. The method of claim 24, wherein said host is cultured under anaerobic, aerobic or micro-aerobic cultivation conditions.

26. The method of claim 24, wherein said host is subjected to a cyclical cultivation strategy to alternate said host between anaerobic cultivation conditions and aerobic cultivation conditions.

27. The method of claim 24, wherein said host is cultured under conditions of nutrient limitation either via nitrogen, phosphate or oxygen limitation.

28. The method of claim 24, wherein the C6 building block is produced by a single microorganism strain via a non-cyclical or cyclical fermentation strategy.

29. The method of claim 24, wherein the C6 building block is produced by co-culturing two or more microorganism strains via a non-cyclical or cyclical fermentation strategy.

30. The method of claim 24, wherein the C6 building block is produced by successive fermentations, wherein the broth or centrate from the preceding fermentation is fed to a succession of fermentations as a source of feedstock, central metabolite, or central precursor; finally producing the C6 building block.

31. The method of claim 24, wherein said recombinant host cells are retained in ceramic hollow fiber membranes to maintain a high cell density during fermentation.

32. The method of claim 25, wherein the principal carbon source fed to the fermentation derives from biological or non-biological feedstocks.

33. The method of claim 25, wherein the host is a prokaryote or a eukaryote.

34. The method of claim 33, wherein the host is a prokaryote from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*.

35. The method of claim 33, wherein the host is a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

36. The method of claim 33, wherein the host's tolerance to high concentrations of a C6 building block is improved through continuous cultivation in a selective environment.

37. The method of claim 33, wherein the host naturally accumulates polyhydroxyalkanoates, and wherein the polymer synthase enzymes are attenuated in the host strain.

38. The method of claim 27, wherein the intracellular concentration of acetyl-CoA for biosynthesis of C6 building blocks is increased in the host by attenuating genes degrading acetyl-CoA.

39. The method of claim 24, wherein an imbalance in NADH is generated that can only be balanced via the formation of a C6 building block.

40. The method of claim 39, wherein a gene encoding a formate dehydrogenase is overexpressed, a gene encoding a pyruvate formate lyase is overexpressed, 2-hydroxybutyrate oxidoreductase activity is attenuated, DL glycerol-3-phosphatase activity is attenuated, and/or malate dehydrogenase activity is attenuated.

41. The method of claim 39, wherein carbon flux is directed into the pentose phosphate cycle in the host by attenuating a glucose-6-phosphate isomerase classified under EC 5.3.1.9.

42. The method of claim 38, wherein a gene encoding an acetate kinase, such as ack, a gene encoding an enzyme that mediates the degradation of pyruvate to lactate such as ldhA, genes encoding enzymes mediating the degradation of phophoenolpyruvate to succinate such as frdBC, a gene encoding an enzyme mediating the degradation of acetyl-CoA to ethanol such as the alcohol dehydrogenase encoded by adhE, a gene encoding an enzyme mediating the degradation of pyruvate to ethanol such as pyruvate decarboxylase, or a gene encoding an enzyme mediating the generation of isobutanol such as a 2-oxoacid decarboxylase is attenuated in the host.

43. The method of claim 24, wherein the intracellular concentration of acetyl-CoA for biosynthesis of a C6 building block is increased in the host by overexpressing genes forming acetyl-CoA.

44. The method of claim 43, wherein an acetyl-CoA synthetase such as the gene product of acs is overexpressed in the host.

45. The method of claim 24, wherein an imbalance in NADPH is generated in the host that can only be balanced via the formation of a C6 building block.

46. The method of claim 45, wherein a puridine nucleotide transhydrogenase gene such as UdhA or a glucose dehydrogenase such as the gene product of gdh is overexpressed in the host.

47. The method of claim 45, wherein a glyceraldehyde-3P-dehydrogenase gene such as GapN is overexpressed in the host, a malic enzyme gene such as maeA or maeB is overexpressed in the host, a glucose-6-phosphate dehydrogenase gene such as zwf is overexpressed in the host, a fructose 1,6 diphosphatase gene such as fbp is overexpressed in the host, activity of a triose phosphate isomerase is attenuated in the host, and/or activity of malate dehydrogenase is attenuated.

48. The method of claim 45, wherein membrane-bound cytochrome P450/ω-hydroxylases are solubilized in the host via truncation of the N-terminal region that anchors the P450 to the endoplasmic reticulum.

49. The method of claim 45, wherein enzymes facilitating the conversion of NADPH to NADH are attenuated in the host or transport of hexanoate to the extracellular media is attenuated.

50. The method of claim 45, wherein the NADH generation cycle that may be generated via inter-conversion of glutamate dehydrogenases in EC 1.4.1.2(NADH-specific) and EC 1.4.1.4(NADPH-specific) is attenuated in the host.

51. The method of claim 45, wherein a glutamate dehydrogenase (EC 1.4.1.3) that utilizes both NADH and NADPH as co-factors is attenuated in the host.

52. The method of claim 24, wherein the degradation of central metabolites leading to the formation of the hexanoyl-CoA is attenuated in the host.

53. The method of claim 52, wherein a propionyl-CoA synthetase such as the gene product of PrpE-RS is overexpressed in the host.

54. The method of claim 52, wherein β-oxidation enzymes degrading central metabolites and central precursors leading to and including C6 building blocks are attenuated in the host.

55. The method of claim 52, wherein enzymes activating C6 building blocks via Coenzyme A esterification such as CoA-ligases are attenuated.

56. The method of claim 24, wherein the efflux of a C6 building block across the cell membrane to the extracellular media is enhanced or amplified by genetically engineering structural modifications to the cell membrane or increasing any associated transporter activity for a C6 building block.

* * * * *